((12)) United States Patent
Draper et al.

(10) Patent No.: US 11,129,839 B2
(45) Date of Patent: Sep. 28, 2021

(54) MINOCYCLINE COMPOUNDS FOR BIODEFENSE

(71) Applicant: Paratek Pharmaceuticals, Inc., Boston, MA (US)

(72) Inventors: Michael P. Draper, Windham, NH (US); S. Ken Tanaka, Bellevue, WA (US)

(73) Assignee: Paratek Pharmaceuticals, Inc., Boston, MA (US)

( * ) Notice: Subject to any disclaimer, the term of this patent is extended or adjusted under 35 U.S.C. 154(b) by 0 days.

(21) Appl. No.: 16/798,500

(22) Filed: Feb. 24, 2020

(65) Prior Publication Data

US 2020/0330489 A1 Oct. 22, 2020

Related U.S. Application Data

(63) Continuation of application No. 15/713,352, filed on Sep. 22, 2017, now abandoned, which is a continuation of application No. PCT/US2016/023807, filed on Mar. 23, 2016.

(60) Provisional application No. 62/137,719, filed on Mar. 24, 2015.

(51) Int. Cl.
*A61K 31/65* (2006.01)
*A61P 31/04* (2006.01)
*A61K 9/00* (2006.01)

(52) U.S. Cl.
CPC ............ *A61K 31/65* (2013.01); *A61K 9/0019* (2013.01); *A61K 9/0053* (2013.01); *A61P 31/04* (2018.01); *Y02A 50/30* (2018.01)

(58) Field of Classification Search
CPC ..................................................... A61K 31/65
See application file for complete search history.

(56) References Cited

U.S. PATENT DOCUMENTS

| 8,440,646 | B1 | 5/2013 | Alekshun et al. |
| 2007/0238652 | A1 | 10/2007 | Kokai-Kun et al. |
| 2008/0233151 | A1 | 9/2008 | Golub et al. |
| 2013/0296228 | A1 | 11/2013 | Patel et al. |
| 2013/0302442 | A1 | 11/2013 | Coulter et al. |
| 2018/0133231 | A1 | 5/2018 | Draper et al. |

FOREIGN PATENT DOCUMENTS

| CN | 102015602 A | 4/2011 |
| JP | 2011-513404 A | 4/2011 |
| WO | 2006/071685 A2 | 7/2006 |
| WO | 2009/111064 A2 | 9/2009 |

OTHER PUBLICATIONS

Draper et al., In Vitro Activity of Omadacycline (OMC) against Biothreat Bacteria. 11th Annual ASM Biodefense and Emerging Diseases Research Meeting. Poster 253(G). 2 pages. Feb. 27, 2013.
Draper et al., Mechanism of action of the novel aminomethylcycline antibiotic omadacycline. Antimicrob Agents Chemother. 2014;58(3):1279-1283.
Macone et al., In vitro and in vivo antibacterial activities of omadacycline, a novel aminomethylcycline. Antimicrob Agents Chemother. 2014;58(2)1127-1135.
Noel et al., A randomized, evaluator-blind, phase 2 study comparing the safety and efficacy of omadacycline to those of linezolid for treatment of complicated skin and skin structure infections. Antimicrob Agents Chemother. Nov. 2012;56 (11):5650-4.
Stundick et al., State-of-the-Art Therapeutic Medical Countermeasures for Bacterial Threat Agents. Drug Development Research. 2011;72:361-378.
International Search Report and Written Opinion for Application No. PCT/US2016/023807, dated Jun. 17, 2016. 8 pages.

*Primary Examiner* — Brian J Davis
(74) *Attorney, Agent, or Firm* — McCarter & English, LLP; Jonathan M. Sparks

(57) ABSTRACT

Methods of treating or preventing a bacterial infection in a subject are disclosed herein, wherein the bacterial infection is caused by a bacterium which can be used as a biological weapon. Also disclosed is a pharmaceutical composition comprising the compound of the present invention for treating or preventing a bacterial infection in a subject, wherein the bacterial infection is caused by a bacterium which can be used as a biological weapon.

18 Claims, 3 Drawing Sheets

MINOCYCLINE COMPOUNDS FOR BIODEFENSE

RELATED APPLICATIONS

This application is a continuation of U.S. patent application Ser. No. 15/713,352, filed on Sep. 22, 2017; which is a continuation of International Patent Application No. PCT/US2016/023807, filed on Mar. 23, 2016; which claims priority to U.S. Provisional Application No. 62/137,719, filed on Mar. 24, 2015. The entire contents of each of the foregoing applications are hereby incorporated herein by reference.

BACKGROUND OF THE INVENTION

Biological agents, including various types of bacteria such as *Bacillus anthracis* and Multi Drug Resistant (MDR) *anthracis*, *Franciscella tularensis*, *Yersinia pestis*, *Burkholderia mallei*, *Burkholderia pseudomallei*, and *Rickettsia prowazekii*, can be used as weapons, which pose a material threat to the national security and public health in the United States. Tetracyclines have proven clinical utilities as antibacterial agents. As a family they have a well-established record of safety and efficacy. Tetracyclines exert their antibacterial effects through multiple routes, including binding to the 30S subunit of the bacterial ribosome and inhibiting the binding of aminoacyl-tRNA. Tetracyclines are known to be active against infections caused by various pathogens. In many cases tetracyclines are indicated for treatment and prophylaxis of diseases caused by these pathogens.

The most prevalent mechanisms of tetracycline resistance among gram-positive and gram-negative bacteria are ribosome protection and efflux. Both mechanisms are readily transferrable among bacterial types as they are often associated with transmissible genetic elements including plasmids, transposons, and integrons, and have been shown to already occur. Therefore, there is a need for effective antibacterial agents for the prevention, prophylaxis, and treatment of infections caused by biological agents, including those that can be used as weapons.

SUMMARY OF THE INVENTION

In some embodiments, the present invention provides a method of treating a bacterial infection in a subject in need thereof, the method comprising administering to the subject an effective amount of a compound, or a salt thereof, at a dose of about 10 mg to about 1000 mg, wherein the compound is Compound A' of the following structural formula:

(A')

wherein the bacterial infection is caused by a bacterium which can be used as a biological weapon, such that the infection in the subject is treated.

In one embodiment, the compound is Compound A of the following structural formula:

(A)

In some aspects, the bacterium is resistant to antibiotics that are typically used to treat infections caused by the bacterium. In a specific aspect, the bacterium is in the form of a powder or an aerosol. In another specific aspect, the bacterium is able to form spores. In some embodiments, the bacterium may be disseminated as spores, or via contamination of food or water supply.

In one embodiment, the bacterium is selected from the group comprising:
a bacterium belonging to the species *Franciscella tularensis*, *Clostridium botulinum*, *Yersinia pestis*, *Burkholderia mallei*, *Burkholderia pseudomallei*, *Coxiella burnetii*, *Chlamydia psittaci*, *Clostridium perfringens*, *Rickettsia prowazekii*, *Campylobacter jejuni*, *Yersinia enterocolitica*, *Listeria monocytogenes*;
a bacterium belonging to the genus *Bacillus* (e.g., *B. anthracis*, including Multi-Drug Resistant (MDR) anthrax strains), *Brucella* (e.g., *B. abortus*, *B. canis*, *B. ceti*, *B. inopinata*, *B. melitensis*, *B. microti*, *B. neotomae*, *B. ovis*, *B. pinnipedialis*, *B. suis*), *Shigella* (e.g., *S. boydii*, *S. dysenteriae*, *S. flexneri* and *S. sonnei*), *Vibrio* (e.g., *V. cholerae*), *Salmonella* (e.g., *S. bongori* and *S. enterica*); and
a bacterium belonging to a diarrheagenic strain of *E. coli*.
In another embodiment, the bacterium is selected from the group comprising:
a bacterium belonging to the species *Franciscella tularensis*, *Yersinia pestis*, *Burkholderia mallei*, *Burkholderia pseudomallei*, *Rickettsia prowazekii*; and
a bacterium belonging to the genus *Bacillus* (e.g., *B. anthracis*, including Multi-Drug Resistant (MDR) anthrax strains).

In some embodiments, the bacterium is selected from the group consisting of:
a bacterium belonging to the species *Franciscella tularensis*, *Clostridium botulinum*, *Yersinia pestis*, *Burkholderia mallei*, *Burkholderia pseudomallei*, *Coxiella burnetii*, *Chlamydia psittaci*, *Clostridium perfringens*, *Rickettsia prowazekii*, *Campylobacter jejuni*, *Yersinia enterocolitica*, *Listeria monocytogenes*;
a bacterium belonging to the genus *Bacillus* (e.g., *B. anthracis*, including Multi-Drug Resistant (MDR) anthrax strains), *Brucella* (e.g., *B. abortus*, *B. canis*, *B. ceti*, *B. inopinata*, *B. melitensis*, *B. microti*, *B. neotomae*, *B. ovis*, *B. pinnipedialis*, *B. suis*), *Shigella* (e.g., *S. boydii*, *S. dysenteriae*, *S. flexneri* and *S. sonnei*), *Vibrio* (e.g., *V. cholerae*), *Salmonella* (e.g., *S. bongori* and *S. enterica*); and
a bacterium belonging to a diarrheagenic strain of *E. coli*.
In yet another embodiment, the bacterium is selected from the group consisting of:
a bacterium belonging to the species *Franciscella tularensis*, *Yersinia pestis*, *Burkholderia mallei*, *Burkholderia pseudomallei*, *Rickettsia prowazekii*; and a bacterium belonging to the genus *Bacillus* (e.g., *B. anthracis*, including Multi-Drug Resistant (MDR) anthrax strains).

In yet another embodiment, the bacterium is selected from the group consisting of: *Yersinia pestis*, *Burkholderia mallei* and *Bacillus anthracia*.

In one embodiment, the compound is administered once per day or twice per day.

In some embodiments, the compound is administered intravenously or orally.

In an embodiment, the compound is administered intravenously at the dose of about 50 mg to about 200 mg. In a further embodiment, the compound is administered at the dose of about 100 mg.

In another embodiment, the compound is administered orally at the dose of about 100 to about 300 mg.

In certain aspects, the method of the invention comprises administering the compound, e.g., Compound A' or Compound A, for at least 3 days, at least 7 days, at least 14 days, at least 21 days, at least 30 days or at least 60 days. In a specific embodiment, the method comprises administering the compound for about 30 days or about 60 days.

In some embodiments, the method comprises administering to the subject one or more loading doses of the compound, followed by one or more maintenance doses of the compound. In one embodiment, the one or more loading dose may be greater than the one or more maintenance dose.

In a specific embodiment, the loading dose is an intravenous dose and the maintenance dose is an oral dose. In another specific embodiment, the loading dose is an intravenous dose and the maintenance dose is also an intravenous dose. In yet another specific embodiment, the loading dose is an oral dose and the maintenance dose is also an oral dose.

In one embodiment, the subject is a human.

In some embodiments, the present invention also provides a method of preventing a bacterial infection in a subject in need thereof, the method comprising administering to the subject an effective amount of a compound, or a salt thereof, at a dose of about 10 mg to about 1000 mg, wherein the compound is Compound A' of the following structural formula:

(A')

wherein the bacterial infection is caused by a bacterium which can be used as a biological weapon, such that the infection in the subject is prevented.

In one embodiment, the compound is Compound A of the following structural formula:

(A)

In some aspects, the bacterium is resistant to antibiotics that are typically used to treat infections caused by the bacterium. In a specific aspect, the bacterium is in the form of a powder or an aerosol. In another specific aspect, the bacterium is able to form spores.

In one embodiment, the bacterium is selected from the group comprising:

a bacterium belonging to the species *Franciscella tularensis*, *Clostridium botulinum*, *Yersinia pestis*, *Burkholderia mallei*, *Burkholderia pseudomallei*, *Coxiella burnetii*, *Chlamydia psittaci*, *Clostridium perfringens*, *Rickettsia prowazekii*, *Campylobacter jejuni*, *Yersinia enterocolitica*, *Listeria monocytogenes*;

a bacterium belonging to the genus *Bacillus* (e.g., *B. anthracia*, including Multi-Drug Resistant (MDR) anthrax strains), *Brucella* (e.g., *B. abortus*, *B. canis*, *B. ceti*, *B. inopinata*, *B. melitensis*, *B. microti*, *B. neotomae*, *B. ovis*, *B. pinnipedialis*, *B. suis*), Shigella (e.g., *S. boydii*, *S. dysenteriae*, *S. flexneri* and *S. sonnei*), Vibrio (e.g., *V. cholerae*), Salmonella (e.g., *S. bongori* and *S. enterica*); and a bacterium belonging to a diarrheagenic strain of E. coli.

In another embodiment, the bacterium is selected from the group comprising: a bacterium belonging to the species *Franciscella tularensis*, *Yersinia pestis*, *Burkholderia mallei*, *Burkholderia pseudomallei*, *Rickettsia prowazekii*; and a bacterium belonging to the genus *Bacillus* (e.g., *B. anthracis*, including Multi-Drug Resistant (MDR) anthrax strains).

In some embodiments, the bacterium is selected from the group consisting of:

a bacterium belonging to the species *Franciscella tularensis*, *Clostridium botulinum*, *Yersinia pestis*, *Burkholderia mallei*, *Burkholderia pseudomallei*, *Coxiella burnetii*, *Chlamydia psittaci*, *Clostridium perfringens*, *Rickettsia prowazekii*, *Campylobacter jejuni*, *Yersinia enterocolitica*, *Listeria monocytogenes*;

a bacterium belonging to the genus *Bacillus* (e.g., *B. anthracis*, including Multi-Drug Resistant (MDR) anthrax strains), *Brucella* (e.g., *B. abortus*, *B. canis*, *B. ceti*, *B. inopinata*, *B. melitensis*, *B. microti*, *B. neotomae*, *B. ovis*, *B. pinnipedialis*, *B. suis*), Shigella (e.g., *S. boydii*, *S. dysenteriae*, *S. flexneri* and *S. sonnei*), Vibrio (e.g., *V. cholerae*), Salmonella (e.g., *S. bongori* and *S. enterica*); and a bacterium belonging to a diarrheagenic strain of E. coli.

In yet another embodiment, the bacterium is selected from the group consisting of:

a bacterium belonging to the species *Franciscella tularensis*, *Yersinia pestis*, *Burkholderia mallei*, *Burkholderia pseudomallei*, *Rickettsia prowazekii*; and a bacterium belonging to the genus *Bacillus* (e.g., *B. anthracis*, including Multi-Drug Resistant (MDR) anthrax strains).

In yet another embodiment, the bacterium is selected from the group consisting of: *Yersinia pestis*, *Burkholderia mallei* and *Bacillus anthracis*.

In some aspects, the dose is about 50 mg to about 200 mg, e.g., about 75 mg to about 110 mg. In one aspect, the dose is about 100 mg.

In one embodiment, the compound is administered once per day or twice per day.

In another embodiment, the compound is administered intravenously or orally.

In certain aspects, the method of the invention comprises administering the compound, e.g., Compound A' or Compound A, for at least 3 days, at least 7 days, at least 14 days, at least 21 days, at least 30 days or at least 60 days. In a specific embodiment, the method comprises administering the compound for about 30 days or about 60 days.

In some embodiments, the method comprises administering to the subject one or more loading doses of the compound, followed by one or more maintenance doses of the compound. In one embodiment, the one or more loading dose may be greater than the one or more maintenance dose.

In a specific embodiment, the loading dose is an intravenous dose and the maintenance dose is an oral dose. In another specific embodiment, the loading dose is an intravenous dose and the maintenance dose is also an intravenous dose. In yet another specific embodiment, the loading dose is an oral dose and the maintenance dose is also an oral dose.

In one embodiment, the subject is a human.

Figure 1:
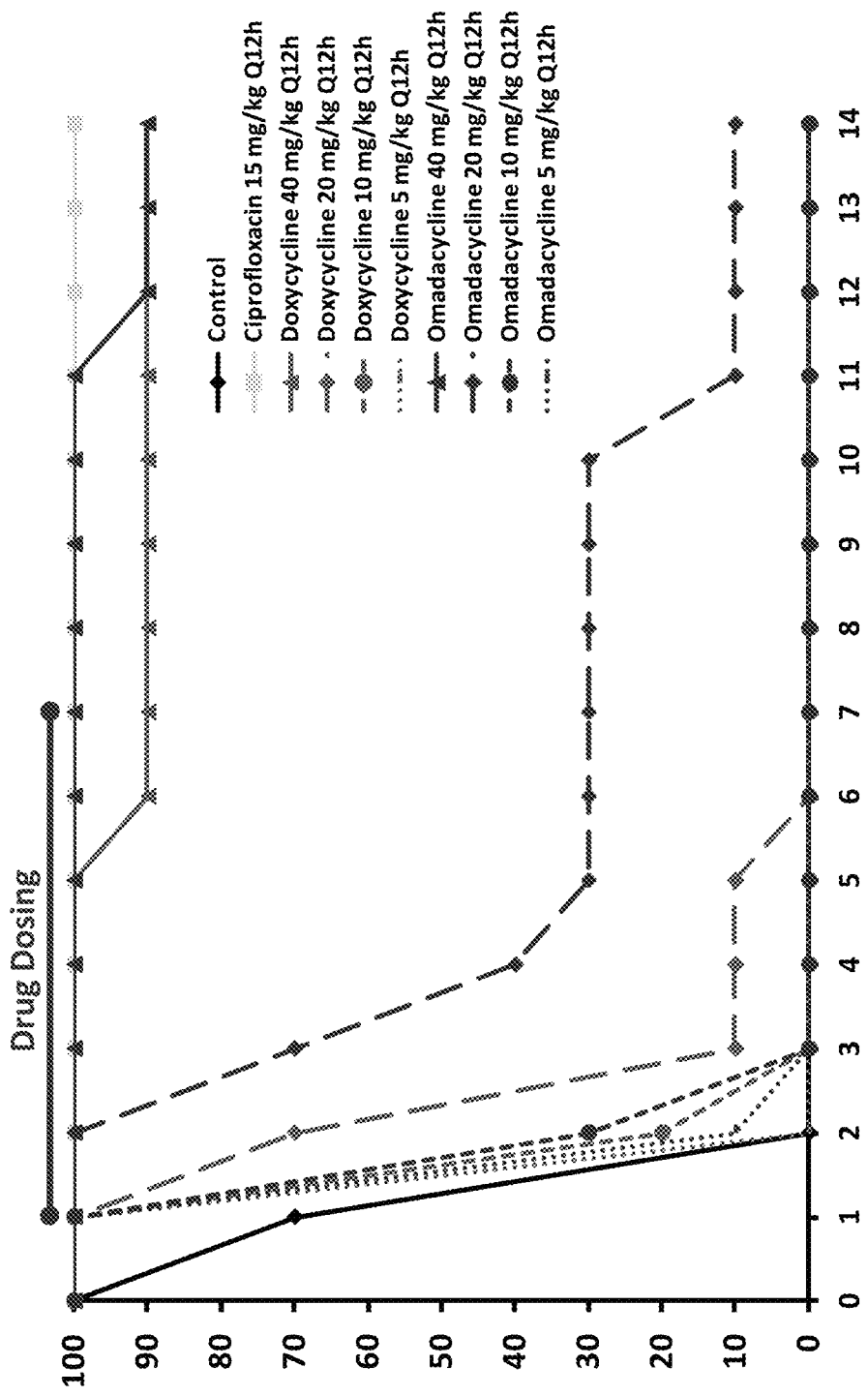
FIG. 1 is a graph showing percent survival in a lethal *Y. pestis* post-exposure prophylactic (PEP) mouse model after treatment with Compound A (omadacycline), doxycycline and ciprofloxacin.

FIG. 2 is a graph showing percent survival in a *B. anthracia* post-exposure prophylactic (PEP) mouse model after treatment with Compound A (omadacycline), doxycycline or ciprofloxacin.

FIG. 3 is a graph showing percent survival in a lethal *B. mallei* post-exposure prophylactic (PEP) mouse model after treatment with Compound A (omadacycline), doxycycline or moxifloxacin.

DETAILED DESCRIPTION OF THE INVENTION

The invention relates to the discovery that 9-[(2,2-dimethyl-propyl amino)-methyl]minocycline (omadacycline, OMC) is effective to treat or prevent infections caused by various types of bacteria that can be used as biological weapons.

In one embodiment, the invention pertains, at least in part, to a method of treating a bacterial infection in a subject, comprising administering to the subject an effective amount of Compound A' or a salt thereof:

(A')

In one embodiment, the invention pertains, at least in part, to a method of treating a bacterial infection in a subject, comprising administering to the subject a compound or a salt thereof, at a dose of about 10 mg to about 1000 mg, wherein the compound is Compound A' of the following structural formula:

(A')

In one embodiment, the invention pertains, at least in part, to a method of preventing a bacterial infection in a subject, comprising administering to the subject an effective amount of Compound A' or a salt thereof:

(A')

In one embodiment, the invention pertains, at least in part, to a method of preventing a bacterial infection in a subject, comprising administering to the subject a compound or a salt thereof, at a dose of about 10 mg to about 1000 mg, wherein the compound is Compound A' of the following structural formula:

(A')

In one embodiment, the invention pertains, at least in part, to a method of treating a bacterial infection in a subject, comprising administering to the subject an effective amount of Compound A or a salt thereof:

(A)

In one embodiment, the invention pertains, at least in part, to a method of treating a bacterial infection in a subject, comprising administering to the subject a compound or a salt thereof, at a dose of about 10 mg to about 1000 mg, wherein the compound is Compound A of the following structural formula:

(A)

In one embodiment, the invention pertains, at least in part, to a method of preventing a bacterial infection in a subject, comprising administering to the subject an effective amount of Compound A or a salt thereof:

(A)

In one embodiment, the invention pertains, at least in part, to a method of preventing a bacterial infection in a subject, comprising administering to the subject a compound or a salt thereof, at a dose of about 10 mg to about 1000 mg, wherein the compound is Compound A of the following structural formula:

(A)

In a particular embodiment, the invention pertains, at least in part, to a method of treating an infection in a subject or preventing an infection in a subject, comprising administering to the subject an effective amount of Compound A' or Compound A, wherein the infection is caused by a bacterium which can be used as a biological weapon.

In one embodiment, a bacterium which can be used as a biological weapon includes a bacterium which possesses one or more of the characteristics, including but not limited to, easily being produced or disseminated, easily being transmitted from person to person, having potential for moderate or high morbidity, having potential for moderate or high mortality, having potential for causing public panic and social disruption, requiring special action for public health preparedness, and requiring specific enhancements for diagnosis and disease surveillance.

In one embodiment, a bacterium which can be used as a biological weapon is stable or viable (e.g., capable of performing all or part of its normal biological functions, such as replicating, forming spores, and infecting a subject) under various conditions (e.g., heat, cold, high pressure, low pressure, acidic or basic conditions, humidity, dryness, and radiation), including extreme conditions. In one embodiment, a bacterium which can be used as a biological weapon is capable of infecting a subject under various conditions. In one embodiment, a bacterium which can be used as a biological weapon is stable or viable under a temperature above 25° C., 30° C., 40° C., 50° C., 60° C., 70° C., 80° C., 90° C., 100° C., 125° C., 150° C., 175° C., or 200° C. In one embodiment, a bacterium which can be used as a biological weapon is stable or viable under a temperature below 25° C., 20° C., 10° C., 5° C., 0° C., −10° C., −20° C., −30° C., −40° C., −50° C., −60° C., −70° C., −100° C., or −150° C. In one embodiment, a bacterium which can be used as a biological weapon is stable or viable under a pressure above $5\times10^5$ Pa, $10\times10^5$ Pa, $15\times10^5$ Pa, $20\times10^5$ Pa, $30\times10^5$ Pa, $40\times10^5$ Pa, $50\times10^5$ Pa, $75\times10^5$ Pa, or $100\times10^5$ Pa. In one embodiment, a bacterium which can be used as a biological weapon is stable or viable under a pressure below $0.5\times10^5$ Pa, $0.2\times10^5$ Pa, $0.1\times10^5$ Pa, $0.05\times10^5$ Pa, $0.02\times10^5$ Pa, $0.01\times10^5$ Pa, $0.005\times10^5$ Pa, $0.002\times10^5$ Pa, or $0.001\times10^5$ Pa. In one embodiment, a bacterium which can be used as a biological weapon is stable or viable under a pH above 8.0, 8.5, 9.0, 9.5, 10.0, 10.5, 11.0, 11.5, 12.0, 12.5, 13.0, 13.5, or 14.0. In one embodiment, a bacterium which can be used as a biological weapon is stable or viable under a pH below 6.0, 5.5, 5.0, 4.5, 4.0, 3.5, 3.0, 2.5, 2.0, 1.5, 1.0, 0.5, or 0.0. In one embodiment, a bacterium which can be used as a biological weapon is stable or viable under a relative humidity of 10%, 20%, 30%, 40%, 50%, 60%, 70%, 75%, 80%, 85%, 90%, 95%, or 99%. In one embodiment, a bacterium which can be used as a biological weapon is stable or viable under f UV radiation, X-ray radiation, α radiation, β radiation, or γ radiation. In another embodiment, the bacterium is capable of infecting a subject after being treated with a combination of any of the aforementioned conditions.

In one embodiment, a bacterium which can be used as a biological weapon is able to form spores.

In one embodiment, the bacterium which can be used as a biological weapon may be disseminated as spores. In another embodiment, the embodiment which can be used as a biological weapon may be disseminated via contamination of food or water supply. In yet another embodiment, the bacterium which can be used as a biological weapon may be disseminated by insects (e.g., fleas, lice and ticks) and/or rodents (e.g., mice or rats).

In one embodiment, a bacterium which can be used as a biological weapon can be dispersed in air or in liquid. In one embodiment, the bacterium is in a form of an aerosol (e.g., the bacterium is formulated as an aerosol). In another embodiment, the bacterium is in a form of powder (e.g., the bacterium is formulated as powder).

In one embodiment, a bacterium which can be used as a biological weapon includes a bacterium which is resistant to existing antibiotics, i.e., antibiotics that are typically used to treat infections caused by the bacterium. In one embodiment, such antibiotics include, e.g., tetracycline antibiotics, including but not limited to tetracycline, doxycycline, minocycline, sancycline, methacycline, chlortetracycline, and deoxytetracycline, and a combination thereof, and other antibiotics, including but not limited to, methicillin, oxacillin, vancomycin, penicillin, linezolid, ciprofloxacin, ceftazidime, and azithromycin. In a further embodiment, a bacterium which can be used as a biological weapon includes a bacterium which is resistant to tetracycline, minocycline, and/or doxycycline.

In one embodiment, a bacterium which can be used as a biological weapon includes, but is not limited to:

a bacterium belonging to the species *Franciscella tularensis, Clostridium botulinum, Yersinia pestis, Burkholderia mallei, Burkholderia pseudomallei, Coxiella burnetii, Chlamydia psittaci, Clostridium perfringens, Rickettsia prowazekii, Campylobacter jejuni, Yersinia enterocolitica, Listeria monocytogenes;* a bacterium belonging to the genus *Bacillus* (e.g., *B. anthracia*, including Multi-Drug Resistant (MDR) anthrax strains), *Brucella* (e.g., *B. abortus, B. canis, B. ceti, B. inopinata, B. melitensis, B. microti, B. neotomae, B. ovis, B. pinnipedialis, B. suis*), *Shigella* (e.g., *S. boydii, S. dysenteriae, S. flexneri* and *S. sonnei*), *Vibrio* (e.g., *V. cholerae, V. parahaemolyticus,* and *V. vulnificus*), *Salmonella* (e.g., *S. bongori* and *S. enterica*); and a bacterium belonging to a diarrheagenic strain of *E. coli.*

In another embodiment, a bacterium which can be used as a biological weapon includes, but is not limited to:

a bacterium belonging to the species *Franciscella tularensis, Clostridium botulinum, Yersinia pestis, Burkholderia mallei, Coxiella burnetii, Chlamydia psittaci, Clostridium perfringens, Rickettsia prowazekii, Campylobacter jejuni, Yersinia enterocolitica, Listeria monocytogenes;* a bacterium belonging to the genus *Bacillus* (e.g., *B. anthracia*, including Multi-Drug Resistant (MDR) anthrax strains), *Brucella* (e.g., *B. abortus, B. canis, B. ceti, B. inopinata, B. melitensis, B. microti, B. neotomae, B. ovis, B. pinnipedialis, B. suis*), *Shigella* (e.g., *S. boydii, S. dysenteriae, S. flexneri* and *S. sonnei*), *Vibrio* (e.g., *V. cholerae, V. parahaemolyticus,* and *V. vulnificus*), *Salmonella* (e.g., *S. bongori* and *S. enterica*); and a bacterium belonging to a diarrheagenic strain of *E. coli.*

In one embodiment, a bacterium which can be used as a biological weapon includes, but is not limited to:

a bacterium belonging to the species *Franciscella tularensis, Clostridium botulinum, Yersinia pestis, Burkholderia mallei, Burkholderia pseudomallei, Coxiella burnetii, Chlamydia psittaci, Clostridium perfringens, Rickettsia prowazekii, Campylobacter jejuni, Yersinia enterocolitica, Listeria monocytogenes;* a bacterium belonging to the genus *Brucella* (e.g., *B. abortus, B. canis, B. ceti, B. inopinata, B. melitensis, B. microti, B. neotomae, B. ovis, B. pinnipedialis, B. suis*), *Shigella* (e.g., *S. boydii, S. dysenteriae, S. flexneri* and *S. sonnei*), *Vibrio* (e.g., *V. cholerae, V. parahaemolyticus,* and *V. vulnificus*), *Salmonella* (e.g., *S. bongori* and *S. enterica*); and a bacterium belonging to a diarrheagenic strain of *E. coli.*

In another embodiment, a bacterium which can be used as a biological weapon includes, but is not limited to:

a bacterium belonging to the species *Franciscella tularensis, Clostridium botulinum, Yersinia pestis, Burkholderia mallei, Coxiella burnetii, Chlamydia psittaci, Clostridium perfringens, Rickettsia prowazekii, Campylobacter jejuni, Yersinia enterocolitica, Listeria monocytogenes;* a bacterium belonging to the genus *Brucella* (e.g., *B. abortus, B. canis, B. ceti, B. inopinata, B. melitensis, B. microti, B. neotomae, B. ovis, B. pinnipedialis, B. suis*), *Shigella* (e.g., *S. boydii, S. dysenteriae, S. flexneri* and *S. sonnei*), *Vibrio* genus (e.g., *V. cholerae, V. parahaemolyticus,* and *V. vulnificus*), *Salmonella* (e.g., *S. bongori* and *S. enterica*); and a bacterium belonging to a diarrheagenic strain of *E. coli.*

In a further embodiment, a bacterium which can be used as a biological weapon includes, but is not limited to:

a bacterium belonging to the species *Franciscella tularensis, Yersinia pestis, Burkholderia mallei, Burkholderia pseudomallei, Rickettsia prowazekii;* and a bacterium belonging to the genus *Bacillus* (e.g., *B. anthracis*, including Multi-Drug Resistant (MDR) anthrax strains).

In a further embodiment, a bacterium which can be used as a biological weapon includes, but is not limited to:

a bacterium belonging to the species *Franciscella tularensis, Yersinia pestis, Burkholderia mallei, Rickettsia prowazekii;* and a bacterium belonging to the *Bacillus* genus (e.g., *B. anthracis*, including Multi-Drug Resistant (MDR) anthrax strains).

In a further embodiment, a bacterium which can be used as a biological weapon includes, but is not limited to, a bacterium belonging to the species *Franciscella tularensis, Yersinia pestis, Burkholderia mallei, Burkholderia pseudomallei,* and *Rickettsia prowazekii*. In a further embodiment, a bacterium which can be used as a biological weapon includes, but is not limited to, a bacterium belonging to the species *Franciscella tularensis, Yersinia pestis, Burkholderia mallei,* and *Rickettsia prowazekii*. In a further embodiment, a bacterium which can be used as a biological weapon is a bacterium belonging to the species *Bacillus anthracis* or a bacterium belonging to a Multi-Drug Resistant (MDR) anthrax strain.

The *Bacillus* genus comprises the species of *Bacillus anthracis* (the etiologic agent of anthrax), *Bacillus cereus, Bacillus weihenstephanensis* (a food borne pathogen), *Bacillus thuringiensis* (an insect pathogen), and *Bacillus mycoides.*

In one embodiment, a bacterium which can be used as a biological weapon includes, but is not limited to, a bacterium of the *Bacillus cereus* group (e.g., *Bacillus anthracis* and Multi-Drug Resistant (MDR) *anthracis*), *Franciscella tularensis, Clostridium botulinum, Yersinia pestis, Burkholderia mallei, Burkholderia pseudomallei, Brucella species, Shigella species, Coxiella burnetii, Chlamydia psittaci, Clostridium perfringens, Rickettsia prowazekii, Diarrheagenic E. coli, Pathogenic Vibrios, Salmonella, Campylobacter jejuni, Yersinia enterocolitica,* and *Listeria monocytogenes.* In one embodiment, a bacterium which can be used as a biological weapon includes, but is not limited to, a bacterium of the *Bacillus cereus* group (e.g., *Bacillus anthracis* and Multi-Drug Resistant (MDR) *anthracis*), *Franciscella tularensis, Clostridium botulinum, Yersinia pestis, Burkholderia mallei, Brucella species, Shigella species, Coxiella burnetii, Chlamydia psittaci, Clostridium perfringens, Rickettsia prowazekii, Diarrheagenic E. coli,*

Pathogenic Vibrios, Salmonella, Campylobacter jejuni, Yersinia enterocolitica, and Listeria monocytogenes.

In one embodiment, a bacterium which can be used as a biological weapon includes, but is not limited to, Franciscella tularensis, Clostridium botulinum, Yersinia pestis, Burkholderia mallei, Burkholderia pseudomallei, Brucella species, Shigella species, Coxiella burnetii, Chlamydia psittaci, Clostridium perfringens, Rickettsia prowazekii, Diarrheagenic E. coli, Pathogenic Vibrios, Salmonella, Campylobacter jejuni, Yersinia enterocolitica, and Listeria monocytogenes. In one embodiment, a bacterium which can be used as a biological weapon includes, but is not limited to, Franciscella tularensis, Clostridium botulinum, Yersinia pestis, Burkholderia mallei, Brucella species, Shigella species, Coxiella burnetii, Chlamydia psittaci, Clostridium perfringens, Rickettsia prowazekii, Diarrheagenic E. coli, Pathogenic Vibrios, Salmonella, Campylobacter jejuni, Yersinia enterocolitica, and Listeria monocytogenes.

In a further embodiment, a bacterium which can be used as a biological weapon includes, but is not limited to, a bacterium of the Bacillus cereus group (e.g., Bacillus anthracis and MultiDrug Resistant (MDR) anthracis), Franciscella tularensis, Yersinia pestis, Burkholderia mallei, Burkholderia pseudomallei, and Rickettsia prowazekii. In a further embodiment, a bacterium which can be used as a biological weapon includes, but is not limited to, a bacterium of the Bacillus cereus group (e.g., Bacillus anthracis and Multi-Drug Resistant (MDR) anthracis), Franciscella tularensis, Yersinia pestis, Burkholderia mallei, and Rickettsia prowazekii.

In a further embodiment, a bacterium which can be used as a biological weapon includes, but is not limited to, Franciscella tularensis, Yersinia pestis, Burkholderia mallei, Burkholderia pseudomallei, and Rickettsia prowazekii. In a further embodiment, a bacterium which can be used as a biological weapon includes, but is not limited to, Franciscella tularensis, Yersinia pestis, Burkholderia mallei, and Rickettsia prowazekii.

In a further embodiment, a bacterium which can be used as a biological weapon is Bacillus anthracis or Multi-Drug Resistant (MDR) anthracis.

Bacillus cereus group of bacteria is composed of Bacillus anthracis (the etiologic agent of anthrax), Bacillus cereus, and Bacillus weihenstephanensis (a food borne pathogen), Bacillus thuringiensis (an insect pathogen), and Bacillus mycoides.

In one embodiment, a bacterium which can be used as a biological weapon does not belong to the species B. anthracis, Y. pestis, F. tularensis, B. mallei or B. pseudomallei. In a specific embodiment, a bacterium which can be used as a biological weapon does not belong to the species B. anthracis. In another embodiment, a bacterium which can be used as a biological weapon does not belong to the species Y. pestis. In another specific embodiment, a bacterium which can be used as a biological weapon does not belong to the species F. tularensis. In another specific embodiment, a bacterium which can be used as a biological weapon does not belong to the species B. mallei. In yet another specific embodiment, a bacterium which can be used as a biological weapon does not belong to the species B. pseudomallei.

In one embodiment, a bacterium which can be used as a biological weapon is not a bacterium that may be a causative agent of a food borne disease. In a specific embodiment, a bacterium which can be used as a biological weapon does not belong to a diarrheagenic strain of E. coli. In another specific embodiment, a bacterium which can be used as a biological weapon does not belong to the genus Salmonella (e.g., S. bongori and S. enterica). In yet another specific embodiment, a bacterium which can be used as a biological weapon does not belong to the species Campylobacter jejuni.

In another embodiment, a bacterium which can be used as a biological weapon is a bacterium that may be a causative agent of a food borne disease. In a specific embodiment, a bacterium which can be used as a biological weapon belongs to a diarrheagenic strain of E. coli. In another specific embodiment, a bacterium which can be used as a biological weapon belongs to the genus Salmonella (e.g., S. bongori and S. enterica). In yet another specific embodiment, a bacterium which can be used as a biological weapon belongs to the species Campylobacter jejuni.

A "food borne disease" or a "food borne illness", or "food poisoning" is any illness resulting from the consumption of food contaminated with, e.g., bacteria. In certain embodiments, the contaminating bacteria may cause an infection and irritation of the gastrointestinal tract. In some embodiments, the contaminating bacteria may belong to a diarrheagenic strain of E. coli; to the species Campylobacter jejuni; or to the genus Salmonella (e.g., S. bongori or S. enterica).

In one embodiment, a bacterium which can be used as a biological weapon includes, but is not limited to, gram-positive pathogens, gram-negative pathogens, anaerobic pathogens, or atypical pathogens, or a combination thereof. In a further embodiment, a bacterium which can be used as a biological weapon includes, but not limited to, a bacterium belonging to the species methicillin-susceptible Staphylococcus aureus (MSSA), methicillin-resistant Staphylococcus aureus (MRSA), oxacillin susceptible Staphylococcus aureus, oxacillin-resistant Staphylococcus aureus, oxacillin-resistant coagulase-negative Staphylococcus, Enterococcus faecalis, Enterococcus faecium, vancomycin susceptible Enterococcus faecium, vancomycin-resistant Enterococcus faecium, vancomycin susceptible Enterococcus faecalis, vancomycin-resistant Enterococcus faecalis, Streptococcus pneumoniae, penicillin-susceptible Streptococcus pneumoniae, penicillin-resistant Streptococcus pneumoniae (PRSP), Streptococcus pyogenes, Streptococcus agalactiae, Haemophilus influenzae, Moraxella catarrhalis, Neisseria gonorrhoeae, Escherichia coli, Shigella spp., Salmonella spp., Klebsiella pneumoniae, Enterobacter aerogenes, Enterobacter cloacae, Serratia marcescens, Acinetobacter baumannii, Stenotrophomonas maltophilia, Bacteroides fragilis, Clostridium perfringens, Chlamydia pneumoniae, Legionella pneumophila, Proteus mirabilis, Pseudomonas aeruginosa, and Burkholderia cepacia.

In one embodiment, the invention pertains, at least in part, to a method of treating a bacterial infection in a subject, comprising administering to the subject an effective amount of Compound A' or a salt thereof:

(A')

[Chemical structure]

wherein the bacterial infection is caused by a bacterium selected from the group consisting of:

a bacterium belonging to the species *Franciscella tularensis, Clostridium botulinum, Yersinia pestis, Burkholderia mallei, Burkholderia pseudomallei, Coxiella burnetii, Chlamydia psittaci, Clostridium perfringens, Rickettsia prowazekii, Campylobacter jejuni, Yersinia enterocolitica, Listeria monocytogenes*;

a bacterium belonging to the genus *Bacillus* (e.g., *B. anthracis*, including Multi-Drug Resistant (MDR) anthrax strains), *Brucella* (e.g., *B. abortus, B. canis, B. ceti, B. inopinata, B. melitensis, B. microti, B. neotomae, B. ovis, B. pinnipedialis, B. suis*), *Shigella* (e.g., *S. boydii, S. dysenteriae, S. flexneri* and *S. sonnei*), *Vibrio* (e.g., *V. cholerae, V. parahaemolyticus*, and *V. vulnificus*), *Salmonella* (e.g., *S. bongori* and *S. enterica*); and a bacterium belonging to a diarrheagenic strain of *E. coli*.

In another embodiment, a bacterium which can be used as a biological weapon is selected from the group consisting of:

a bacterium belonging to the species *Franciscella tularensis, Clostridium botulinum, Yersinia pestis, Burkholderia mallei, Coxiella burnetii, Chlamydia psittaci, Clostridium perfringens, Rickettsia prowazekii, Campylobacter jejuni, Yersinia enterocolitica, Listeria monocytogenes*;

a bacterium belonging to the genus *Bacillus* (e.g., *B. anthracis*, including Multi-Drug Resistant (MDR) anthrax strains), *Brucella* (e.g., *B. abortus, B. canis, B. ceti, B. inopinata, B. melitensis, B. microti, B. neotomae, B. ovis, B. pinnipedialis, B. suis*), *Shigella* (e.g., *S. boydii, S. dysenteriae, S. flexneri* and *S. sonnei*), *Vibrio* (e.g., *V. cholerae, V. parahaemolyticus*, and *V. vulnificus*), *Salmonella* (e.g., *S. bongori* and *S. enterica*); and a bacterium belonging to a diarrheagenic strain of *E. coli*.

In one embodiment, a bacterium which can be used as a biological weapon is selected from the group consisting of:

a bacterium belonging to the species *Franciscella tularensis, Clostridium botulinum, Yersinia pestis, Burkholderia mallei, Burkholderia pseudomallei, Coxiella burnetii, Chlamydia psittaci, Clostridium perfringens, Rickettsia prowazekii, Campylobacter jejuni, Yersinia enterocolitica, Listeria monocytogenes*;

a bacterium belonging to the genus *Brucella* (e.g., *B. abortus, B. canis, B. ceti, B. inopinata, B. melitensis, B. microti, B. neotomae, B. ovis, B. pinnipedialis, B. suis*), *Shigella* (e.g., *S. boydii, S. dysenteriae, S. flexneri* and *S. sonnei*), *Vibrio* (e.g., *V. cholerae, V. parahaemolyticus*, and *V. vulnificus*), *Salmonella* (e.g., *S. bongori* and *S. enterica*); and a bacterium belonging to a diarrheagenic strain of *E. coli*.

In one embodiment, a bacterium which can be used as a biological weapon is selected from the group consisting of:

a bacterium belonging to the species *Franciscella tularensis, Clostridium botulinum, Yersinia pestis, Burkholderia mallei, Coxiella burnetii, Chlamydia psittaci, Clostridium perfringens, Rickettsia prowazekii, Campylobacter jejuni, Yersinia enterocolitica, Listeria monocytogenes*;

a bacterium belonging to the genus *Brucella* (e.g., *B. abortus, B. canis, B. ceti, B. inopinata, B. melitensis, B. microti, B. neotomae, B. ovis, B. pinnipedialis, B. suis*), *Shigella* (e.g., *S. boydii, S. dysenteriae, S. flexneri* and *S. sonnei*), *Vibrio* genus (e.g., *V. cholerae, V. parahaemolyticus*, and *V. vulnificus*), *Salmonella* (e.g., *S. bongori* and *S. enterica*); and a bacterium belonging to a diarrheagenic strain of *E. coli*.

In a further embodiment, a bacterium which can be used as a biological weapon is selected from the group consisting of:

a bacterium belonging to the species *Franciscella tularensis, Yersinia pestis, Burkholderia mallei, Burkholderia pseudomallei, Rickettsia prowazekii*; and a bacterium belonging to the genus *Bacillus* (e.g., *B. anthracis*, including Multi-Drug Resistant (MDR) anthrax strains).

In a further embodiment, a bacterium which can be used as a biological weapon is selected from the group consisting of:

a bacterium belonging to the species *Franciscella tularensis, Yersinia pestis, Burkholderia mallei, Rickettsia prowazekii*; and a bacterium belonging to the *Bacillus* genus (e.g., *B. anthracis*, including Multi-Drug Resistant (MDR) anthrax strains).

In a further embodiment, a bacterium which can be used as a biological weapon is selected from the group consisting of a bacterium belonging to the species *Franciscella tularensis, Yersinia pestis, Burkholderia mallei, Burkholderia pseudomallei*, and *Rickettsia prowazekii*. In a further embodiment, a bacterium which can be used as a biological weapon is selected from the group consisting of a bacterium belonging to the species *Franciscella tularensis, Yersinia pestis, Burkholderia mallei*, and *Rickettsia prowazekii*. In another embodiment, a bacterium which can be used as a biological weapon is a bacterium belonging to the species *Bacillus anthracis* or a bacterium belonging to a Multi-Drug Resistant (MDR) anthrax strain.

In one embodiment, a bacterium which can be used as a biological weapon does not belong to the species *B. anthracis, Y. pestis, F. tularensis, B. mallei* or *B. pseudomallei*. In a specific embodiment, a bacterium which can be used as a biological weapon does not belong to the species *B. anthracis*. In another embodiment, a bacterium which can be used as a biological weapon does not belong to the species *Y. pestis*. In another specific embodiment, a bacterium which can be used as a biological weapon does not belong to the species *F. tularensis*. In another specific embodiment, a bacterium which can be used as a biological weapon does not belong to the species *B. mallei*. In yet another specific embodiment, a bacterium which can be used as a biological weapon does not belong to the species *B. pseudomallei*.

In one embodiment, a bacterium which can be used as a biological weapon is not a bacterium that may be a causative agent of a food borne disease. In a specific embodiment, a bacterium which can be used as a biological weapon does not belong to a diarrheagenic strain of *E. coli*. In another specific embodiment, a bacterium which can be used as a biological weapon does not belong to the genus *Salmonella* (e.g., *S. bongori* and *S. enterica*). In yet another specific embodiment, a bacterium which can be used as a biological weapon does not belong to the species *Campylobacter jejuni*.

It will be understood that for all listed embodiments the compound of the invention, e.g., Compound A', may be administered at a dose of about 10 mg to about 1000 mg.

In one embodiment, the invention pertains, at least in part, to a method of preventing a bacterial infection in a subject, comprising administering to the subject an effective amount of Compound A' or a salt thereof:

(A')

[Chemical structure of a tetracycline derivative]

wherein the bacterial infection is caused by a bacterium selected from the group consisting of:

a bacterium belonging to the species *Franciscella tularensis, Clostridium botulinum, Yersinia pestis, Burkholderia mallei, Burkholderia pseudomallei, Coxiella burnetii, Chlamydia psittaci, Clostridium perfringens, Rickettsia prowazekii, Campylobacter jejuni, Yersinia enterocolitica, Listeria monocytogenes;* a bacterium belonging to the genus *Bacillus* (e.g., *B. anthracia*, including Multi-Drug Resistant (MDR) anthrax strains), *Brucella* (e.g., *B. abortus, B. canis, B. ceti, B. inopinata, B. melitensis, B. microti, B. neotomae, B. ovis, B. pinnipedialis, B. suis), Shigella* (e.g., *S. boydii, S. dysenteriae, S. flexneri* and *S. sonnei), Vibrio* (e.g., *V. cholerae, V. parahaemolyticus*, and *V. vulnificus), Salmonella* (e.g., *S. bongori* and *S. enterica);* and a bacterium belonging to a diarrheagenic strain of *E. coli*.

In another embodiment, a bacterium which can be used as a biological weapon is selected from the group consisting of:

a bacterium belonging to the species *Franciscella tularensis, Clostridium botulinum, Yersinia pestis, Burkholderia mallei, Coxiella burnetii, Chlamydia psittaci, Clostridium perfringens, Rickettsia prowazekii, Campylobacter jejuni, Yersinia enterocolitica, Listeria monocytogenes;* a bacterium belonging to the genus *Bacillus* (e.g., *B. anthracis*, including Multi-Drug Resistant (MDR) anthrax strains), *Brucella* (e.g., *B. abortus, B. canis, B. ceti, B. inopinata, B. melitensis, B. microti, B. neotomae, B. ovis, B. pinnipedialis, B. suis), Shigella* (e.g., *S. boydii, S. dysenteriae, S. flexneri* and *S. sonnei), Vibrio* (e.g., *V. cholerae, V. parahaemolyticus*, and *V. vulnificus), Salmonella* (e.g., *S. bongori* and *S. enterica);* and a bacterium belonging to a diarrheagenic strain of *E. coli*.

In one embodiment, a bacterium which can be used as a biological weapon is selected from the group consisting of:

a bacterium belonging to the species *Franciscella tularensis, Clostridium botulinum, Yersinia pestis, Burkholderia mallei, Burkholderia pseudomallei, Coxiella burnetii, Chlamydia psittaci, Clostridium perfringens, Rickettsia prowazekii, Campylobacter jejuni, Yersinia enterocolitica, Listeria monocytogenes;* a bacterium belonging to the genus *Brucella* (e.g., *B. abortus, B. canis, B. ceti, B. inopinata, B. melitensis, B. microti, B. neotomae, B. ovis, B. pinnipedialis, B. suis), Shigella* (e.g., *S. boydii, S. dysenteriae, S. flexneri* and *S. sonnei), Vibrio* (e.g., *V. cholerae, V. parahaemolyticus*, and *V. vulnificus), Salmonella* (e.g., *S. bongori* and *S. enterica);* and a bacterium belonging to a diarrheagenic strain of *E. coli*.

In one embodiment, a bacterium which can be used as a biological weapon is selected from the group consisting of:

a bacterium belonging to the species *Franciscella tularensis, Clostridium botulinum, Yersinia pestis, Burkholderia mallei, Coxiella burnetii, Chlamydia psittaci, Clostridium perfringens, Rickettsia prowazekii, Campylobacter jejuni, Yersinia enterocolitica, Listeria monocytogenes;* a bacterium belonging to the genus *Brucella* (e.g., *B. abortus, B. canis, B. ceti, B. inopinata, B. melitensis, B. microti, B. neotomae, B. ovis, B. pinnipedialis, B. suis), Shigella* (e.g., *S. boydii, S. dysenteriae, S. flexneri* and *S. sonnei), Vibrio* genus (e.g., *V. cholerae, V. parahaemolyticus*, and *V. vulnificus), Salmonella* (e.g., *S. bongori* and *S. enterica);* and a bacterium belonging to a diarrheagenic strain of *E. coli*.

In a further embodiment, a bacterium which can be used as a biological weapon is selected from the group consisting of:

a bacterium belonging to the species *Franciscella tularensis, Yersinia pestis, Burkholderia mallei, Burkholderia pseudomallei, Rickettsia prowazekii;* and a bacterium belonging to the genus *Bacillus* (e.g., *B. anthracis*, including Multi-Drug Resistant (MDR) anthrax strains).

In a further embodiment, a bacterium which can be used as a biological weapon is selected from the group consisting of:

a bacterium belonging to the species *Franciscella tularensis, Yersinia pestis, Burkholderia mallei, Rickettsia prowazekii;* and a bacterium belonging to the *Bacillus* genus (e.g., *B. anthracis*, including Multi-Drug Resistant (MDR) anthrax strains).

In a further embodiment, a bacterium which can be used as a biological weapon is selected from the group consisting of a bacterium belonging to the species *Franciscella tularensis, Yersinia pestis, Burkholderia mallei, Burkholderia pseudomallei,* and *Rickettsia prowazekii*. In a further embodiment, a bacterium which can be used as a biological weapon is selected from the group consisting of a bacterium belonging to the species *Franciscella tularensis, Yersinia pestis, Burkholderia mallei,* and *Rickettsia prowazekii*. In another embodiment, a bacterium which can be used as a biological weapon is a bacterium belonging to the species *Bacillus anthracis* or a bacterium belonging to a Multi-Drug Resistant (MDR) anthrax strain.

In one embodiment, a bacterium which can be used as a biological weapon does not belong to the species *B. anthracis, Y. pestis, F. tularensis, B. mallei* or *B. pseudomallei*. In a specific embodiment, a bacterium which can be used as a biological weapon does not belong to the species *B. anthracis*. In another embodiment, a bacterium which can be used as a biological weapon does not belong to the species *Y. pestis*. In another specific embodiment, a bacterium which can be used as a biological weapon does not belong to the species *F. tularensis*. In another specific embodiment, a bacterium which can be used as a biological weapon does not belong to the species *B. mallei*. In yet another specific embodiment, a bacterium which can be used as a biological weapon does not belong to the species *B. pseudomallei*.

In one embodiment, a bacterium which can be used as a biological weapon is not a bacterium that may be a causative agent of a food borne disease. In a specific embodiment, a bacterium which can be used as a biological weapon does not belong to a diarrheagenic strain of *E. coli*. In another specific embodiment, a bacterium which can be used as a biological weapon does not belong to the genus *Salmonella* (e.g., *S. bongori* and *S. enterica*). In yet another specific embodiment, a bacterium which can be used as a biological weapon does not belong to the species *Campylobacter jejuni*.

It will be understood that for all listed embodiments the compound of the invention, e.g., Compound A' may be administered at a dose of about 10 mg to about 1000 mg.

In one embodiment, the invention pertains, at least in part, to a method of treating a bacterial infection in a subject, comprising administering to the subject an effective amount of Compound A or a salt thereof:

(A)

wherein the bacterial infection is caused by a bacterium selected from the group consisting of:

a bacterium belonging to the species *Franciscella tularensis, Clostridium botulinum, Yersinia pestis, Burkholderia mallei, Burkholderia pseudomallei, Coxiella burnetii, Chlamydia psittaci, Clostridium perfringens, Rickettsia prowazekii, Campylobacter jejuni, Yersinia enterocolitica, Listeria monocytogenes;* a bacterium belonging to the genus *Bacillus* (e.g., *B. anthracis*, including Multi-Drug Resistant (MDR) anthrax strains), *Brucella* (e.g., *B. abortus, B. canis, B. ceti, B. inopinata, B. melitensis, B. microti, B. neotomae, B. ovis, B. pinnipedialis, B. suis*), *Shigella* (e.g., *S. boydii, S. dysenteriae, S. flexneri* and *S. sonnei*), *Vibrio* (e.g., *V. cholerae, V. parahaemolyticus*, and *V. vulnificus*), *Salmonella* (e.g., *S. bongori* and *S. enterica*); and a bacterium belonging to a diarrheagenic strain of *E. coli.*

In another embodiment, a bacterium which can be used as a biological weapon is selected from the group consisting of:

a bacterium belonging to the species *Franciscella tularensis, Clostridium botulinum, Yersinia pestis, Burkholderia mallei, Coxiella burnetii, Chlamydia psittaci, Clostridium perfringens, Rickettsia prowazekii, Campylobacter jejuni, Yersinia enterocolitica, Listeria monocytogenes;* a bacterium belonging to the genus *Bacillus* (e.g., *B. anthracis*, including Multi-Drug Resistant (MDR) anthrax strains), *Brucella* (e.g., *B. abortus, B. canis, B. ceti, B. inopinata, B. melitensis, B. microti, B. neotomae, B. ovis, B. pinnipedialis, B. suis*), *Shigella* (e.g., *S. boydii, S. dysenteriae, S. flexneri* and *S. sonnei*), *Vibrio* (e.g., *V. cholerae, V. parahaemolyticus*, and *V. vulnificus*), *Salmonella* (e.g., *S. bongori* and *S. enterica*); and a bacterium belonging to a diarrheagenic strain of *E. coli.*

In one embodiment, a bacterium which can be used as a biological weapon is selected from the group consisting of:

a bacterium belonging to the species *Franciscella tularensis, Clostridium botulinum, Yersinia pestis, Burkholderia mallei, Burkholderia pseudomallei, Coxiella burnetii, Chlamydia psittaci, Clostridium perfringens, Rickettsia prowazekii, Campylobacter jejuni, Yersinia enterocolitica, Listeria monocytogenes;* a bacterium belonging to the genus *Brucella* (e.g., *B. abortus, B. canis, B. ceti, B. inopinata, B. melitensis, B. microti, B. neotomae, B. ovis, B. pinnipedialis, B. suis*), *Shigella* (e.g., *S. boydii, S. dysenteriae, S. flexneri* and *S. sonnei*), *Vibrio* (e.g., *V. cholerae, V. parahaemolyticus,* and *V. vulnificus*), *Salmonella* (e.g., *S. bongori* and *S. enterica*); and a bacterium belonging to a diarrheagenic strain of *E. coli.*

In one embodiment, a bacterium which can be used as a biological weapon is selected from the group consisting of:

a bacterium belonging to the species *Franciscella tularensis, Clostridium botulinum, Yersinia pestis, Burkholderia mallei, Coxiella burnetii, Chlamydia psittaci, Clostridium perfringens, Rickettsia prowazekii, Campylobacter jejuni, Yersinia enterocolitica, Listeria monocytogenes;* a bacterium belonging to the genus *Brucella* (e.g., *B. abortus, B. canis, B. ceti, B. inopinata, B. melitensis, B. microti, B. neotomae, B. ovis, B. pinnipedialis, B. suis*), *Shigella* (e.g., *S. boydii, S. dysenteriae, S. flexneri* and *S. sonnei*), *Vibrio* genus (e.g., *V. cholerae, V. parahaemolyticus,* and *V. vulnificus*), *Salmonella* (e.g., *S. bongori* and *S. enterica*); and a bacterium belonging to a diarrheagenic strain of *E. coli.*

In a further embodiment, a bacterium which can be used as a biological weapon is selected from the group consisting of:

a bacterium belonging to the species *Franciscella tularensis, Yersinia pestis, Burkholderia mallei, Burkholderia pseudomallei, Rickettsia prowazekii*; and a bacterium belonging to the genus *Bacillus* (e.g., *B. anthracis*, including Multi-Drug Resistant (MDR) anthrax strains).

In a further embodiment, a bacterium which can be used as a biological weapon is selected from the group consisting of:

a bacterium belonging to the species *Franciscella tularensis, Yersinia pestis, Burkholderia mallei, Rickettsia prowazekii*; and a bacterium belonging to the *Bacillus* genus (e.g., *B. anthracis*, including Multi-Drug Resistant (MDR) anthrax strains).

In a further embodiment, a bacterium which can be used as a biological weapon is selected from the group consisting of a bacterium belonging to the species *Franciscella tularensis, Yersinia pestis, Burkholderia mallei, Burkholderia pseudomallei*, and *Rickettsia prowazekii*. In a further embodiment, a bacterium which can be used as a biological weapon is selected from the group consisting of a bacterium belonging to the species *Franciscella tularensis, Yersinia pestis, Burkholderia mallei*, and *Rickettsia prowazekii*. In another embodiment, a bacterium which can be used as a biological weapon is a bacterium belonging to the species *Bacillus anthracis* or a bacterium belonging to a Multi-Drug Resistant (MDR) anthrax strain.

In one embodiment, a bacterium which can be used as a biological weapon does not belong to the species *B. anthracis, Y. pestis, F. tularensis, B. mallei* or *B. pseudomallei*. In a specific embodiment, a bacterium which can be used as a biological weapon does not belong to the species *B. anthracis*. In another embodiment, a bacterium which can be used as a biological weapon does not belong to the species *Y. pestis*. In another specific embodiment, a bacterium which can be used as a biological weapon does not belong to the species *F. tularensis*. In another specific embodiment, a bacterium which can be used as a biological weapon does not belong to the species *B. mallei*. In yet another specific embodiment, a bacterium which can be used as a biological weapon does not belong to the species *B. pseudomallei.*

In one embodiment, a bacterium which can be used as a biological weapon is not a bacterium that may be a causative agent of a food borne disease. In a specific embodiment, a bacterium which can be used as a biological weapon does not belong to a diarrheagenic strain of *E. coli*. In another specific embodiment, a bacterium which can be used as a biological weapon does not belong to the genus *Salmonella* (e.g., *S. bongori* and *S. enterica*). In yet another specific embodiment, a bacterium which can be used as a biological weapon does not belong to the species *Campylobacter jejuni*.

It will be understood that for all listed embodiments the compound of the invention, e.g., Compound A, may be administered at a dose of about 10 mg to about 1000 mg.

In one embodiment, the invention pertains, at least in part, to a method of preventing a bacterial infection in a subject, comprising administering to the subject an effective amount of Compound A or a salt thereof:

(A)

wherein the bacterial infection is caused by a bacterium selected from the group consisting of:

a bacterium belonging to the species *Franciscella tularensis, Clostridium botulinum, Yersinia pestis, Burkholderia mallei, Burkholderia pseudomallei, Coxiella burnetii, Chlamydia psittaci, Clostridium perfringens, Rickettsia prowazekii, Campylobacter jejuni, Yersinia enterocolitica, Listeria monocytogenes*;

a bacterium belonging to the genus *Bacillus* (e.g., *B. anthracia*, including Multi-Drug Resistant (MDR) anthrax strains), *Brucella* (e.g., *B. abortus, B. canis, B. ceti, B. inopinata, B. melitensis, B. microti, B. neotomae, B. ovis, B. pinnipedialis, B. suis*), *Shigella* (e.g., *S. boydii, S. dysenteriae, S. flexneri* and *S. sonnei*), *Vibrio* (e.g., *V. cholerae, V. parahaemolyticus*, and *V. vulnificus*), *Salmonella* (e.g., *S. bongori* and *S. enterica*); and a bacterium belonging to a diarrheagenic strain of *E. coli*.

In another embodiment, a bacterium which can be used as a biological weapon is selected from the group consisting of:

a bacterium belonging to the species *Franciscella tularensis, Clostridium botulinum, Yersinia pestis, Burkholderia mallei, Coxiella burnetii, Chlamydia psittaci, Clostridium perfringens, Rickettsia prowazekii, Campylobacter jejuni, Yersinia enterocolitica, Listeria monocytogenes*;

a bacterium belonging to the genus *Bacillus* (e.g., *B. anthracia*, including Multi-Drug Resistant (MDR) anthrax strains), *Brucella* (e.g., *B. abortus, B. canis, B. ceti, B. inopinata, B. melitensis, B. microti, B. neotomae, B. ovis, B. pinnipedialis, B. suis*), *Shigella* (e.g., *S. boydii, S. dysenteriae, S. flexneri* and *S. sonnei*), *Vibrio* (e.g., *V. cholerae, V. parahaemolyticus*, and *V. vulnificus*), *Salmonella* (e.g., *S. bongori* and *S. enterica*); and a bacterium belonging to a diarrheagenic strain of *E. coli*.

In one embodiment, a bacterium which can be used as a biological weapon is selected from the group consisting of:

a bacterium belonging to the species *Franciscella tularensis, Clostridium botulinum, Yersinia pestis, Burkholderia mallei, Burkholderia pseudomallei, Coxiella burnetii, Chlamydia psittaci, Clostridium perfringens, Rickettsia prowazekii, Campylobacter jejuni, Yersinia enterocolitica, Listeria monocytogenes*;

a bacterium belonging to the genus *Brucella* (e.g., *B. abortus, B. canis, B. ceti, B. inopinata, B. melitensis, B. microti, B. neotomae, B. ovis, B. pinnipedialis, B. suis*), *Shigella* (e.g., *S. boydii, S. dysenteriae, S. flexneri* and *S. sonnei*), *Vibrio* (e.g., *V. cholerae, V. parahaemolyticus*, and *V. vulnificus*), *Salmonella* (e.g., *S. bongori* and *S. enterica*); and a bacterium belonging to a diarrheagenic strain of *E. coli*.

In one embodiment, a bacterium which can be used as a biological weapon is selected from the group consisting of:

a bacterium belonging to the species *Franciscella tularensis, Clostridium botulinum, Yersinia pestis, Burkholderia mallei, Coxiella burnetii, Chlamydia psittaci, Clostridium perfringens, Rickettsia prowazekii, Campylobacter jejuni, Yersinia enterocolitica, Listeria monocytogenes*;

a bacterium belonging to the genus *Brucella* (e.g., *B. abortus, B. canis, B. ceti, B. inopinata, B. melitensis, B. microti, B. neotomae, B. ovis, B. pinnipedialis, B. suis*), *Shigella* (e.g., *S. boydii, S. dysenteriae, S. flexneri* and *S. sonnei*), *Vibrio* genus (e.g., *V. cholerae, V. parahaemolyticus*, and *V. vulnificus*), *Salmonella* (e.g., *S. bongori* and *S. enterica*); and a bacterium belonging to a diarrheagenic strain of *E. coli*.

In a further embodiment, a bacterium which can be used as a biological weapon is selected from the group consisting of:

a bacterium belonging to the species *Franciscella tularensis, Yersinia pestis, Burkholderia mallei, Burkholderia pseudomallei, Rickettsia prowazekii*; and a bacterium belonging to the genus *Bacillus* (e.g., *B. anthracis*, including Multi-Drug Resistant (MDR) anthrax strains).

In a further embodiment, a bacterium which can be used as a biological weapon is selected from the group consisting of:

a bacterium belonging to the species *Franciscella tularensis, Yersinia pestis, Burkholderia mallei, Rickettsia prowazekii*; and a bacterium belonging to the Bacillus genus (e.g., *B. anthracis*, including Multi-Drug Resistant (MDR) anthrax strains).

In a further embodiment, a bacterium which can be used as a biological weapon is selected from the group consisting of a bacterium belonging to the species *Franciscella tularensis, Yersinia pestis, Burkholderia mallei, Burkholderia pseudomallei*, and *Rickettsia prowazekii*. In a further embodiment, a bacterium which can be used as a biological weapon is selected from the group consisting of a bacterium belonging to the species *Franciscella tularensis, Yersinia pestis, Burkholderia mallei*, and *Rickettsia prowazekii*. In another embodiment, a bacterium which can be used as a biological weapon is a bacterium belonging to the species *Bacillus anthracis* or a bacterium belonging to a Multi-Drug Resistant (MDR) anthrax strain.

In one embodiment, a bacterium which can be used as a biological weapon does not belong to the species *B. anthracis, Y. pestis, F. tularensis, B. mallei* or *B. pseudomallei*. In a specific embodiment, a bacterium which can be used as a biological weapon does not belong to the species *B. anthracis*. In another embodiment, a bacterium which can be used as a biological weapon does not belong to the species *Y. pestis*. In another specific embodiment, a bacterium which can be used as a biological weapon does not belong to the species *F. tularensis*. In another specific embodiment, a bacterium which can be used as a biological weapon does not belong to the species *B. mallei*. In yet another specific embodiment, a bacterium which can be used as a biological weapon does not belong to the species *B. pseudomallei*.

In one embodiment, a bacterium which can be used as a biological weapon is not a bacterium that may be a causative agent of a food borne disease. In a specific embodiment, a bacterium which can be used as a biological weapon does not belong to a diarrheagenic strain of *E. coli*. In another specific embodiment, a bacterium which can be used as a biological weapon does not belong to the genus *Salmonella* (e.g., *S. bongori* and *S. enterica*). In yet another specific embodiment, a bacterium which can be used as a biological weapon does not belong to the species *Campylobacter jejuni*.

It will be understood that for all listed embodiments the compound of the invention, e.g., Compound A, may be administered at a dose of about 10 mg to about 1000 mg.

In one embodiment, treating a bacterial infection in a subject comprises administering the compound of the present invention after the subject's exposure to the bacterium, but before the subject develops a symptom of the bacterial infection. In one embodiment, the compound of the present invention is administered 10 min, 20 min, 30 min, 40 min, 50 min, 1 hr, 2 hrs, 3 hrs, 6 hrs, 12 hrs, 18 hrs, 24 hrs, 36 hrs, 48 hrs, 72 hrs, 96 hrs, 1 week, or 2 weeks after the subject's exposure but before the subject develops a symptom of the bacterial infection.

In another embodiment, treating a bacterial infection in a subject comprises administering the compound of the present invention after the subject develops a symptom after the subject's exposure to the bacterium. In one embodiment, the compound of the present invention is administered 10 min, 20 min, 30 min, 40 min, 50 min, 1 hr, 2 hrs,3 hrs, 6 hrs, 12 hrs, 18 hrs, 24 hrs, 36 hrs, 48 hrs, 72 hrs, 96 hrs, 1 week, or 2 weeks after the subject develops a symptom of the bacterial infection.

In another embodiment, treating a bacterial infection in a subject comprises administering the compound of the present invention after the subject's suspected exposure to the bacterium, but before the subject develops any symptom of the bacterial infection. In one embodiment, the compound of the present invention is administered 10 min, 20 min, 30 min, 40 min, 50 min, 1 hr, 2 hrs, 3 hrs, 6 hrs, 12 hrs, 18 hrs, 24 hrs, 36 hrs, 48 hrs, 72 hrs, 96 hrs, 1 week, or 2 weeks after the subject's suspected exposure but before the subject develops any symptom.

"Suspected exposure" means that there is certain possibility (e.g., 5%, 10%, 20%, 30%, 40%, 50%, 60%, 70%, 75%, 80%, 85%, 90%, 95%, or 99%), although it is not known, that a subject has been exposed to a bacterium and thus is at the risk of a bacterial infection. In some embodiments, "suspected exposure" refers to a chance of greater than 5%, 10%, 20%, 30%, 40%, 50%, 60%, 70%, 75%, 80%, 85%, 90%, 95%, or 99% that the subject has been exposed to a bacterial and is therefore at a risk of a bacterial infection. For example, "suspected exposure" means that there is greater than 50% possibility that a subject has been exposed to a bacterium.

A "symptom" of a bacterial infection can be any indication that the subject being exposed or suspected being exposed to the bacterium is not normal, well, or comfortable, regardless of the subject's subjective perception or feeling. "Symptom" includes, but is not limited to, headache, stomachache, abdominal cramps, abdominal pain, muscle pain, fever, diarrhea, vomiting, coughing, weakness, tiredness, soreness, rash or bumps on skin, wounds in any parts of the body (e.g., skin, head, eye, ear, nose, mouth, torso, limbs, arm, hand, leg, foot, etc.), and an abnormality in any tissue or organ (e.g., skin, bone, blood, lymph, intestine, stomach, pancreas, brain, heart, lung, liver, spleen, kidney, bladder, ovary, etc.).

In one embodiment, preventing a bacterial infection in a subject comprises administering the compound of the present invention before the subject's exposure to the bacterium. In one embodiment, the compound of the present invention is administered 10 min, 20 min, 30 min, 40 min, 50 min, 1 hr, 2 hrs, 3 hrs, 6 hrs, 12 hrs, 18 hrs, 24 hrs, 36 hrs, 48 hrs, 72 hrs, 96 hrs, 1 week, or 2 weeks before the subject's exposure. In another embodiment, preventing a bacterial infection in a subject comprises administering the compound of the present invention before or after an event which raises the risk of the subject being exposed to the bacterium. The event includes, but is not limited to, a terrorist attack with a biological weapon and the subject's entry into a risky territory, such as a battlefield. In one embodiment, the compound of the present invention is administered to the subject 10 min, 20 min, 30 min, 40 min, 50 min, 1 hr, 2 hrs, 3 hrs, 6 hrs, 12 hrs, 18 hrs, 24 hrs, 36 hrs, 48 hrs, 72 hrs, 96 hrs, 1 week, or 2 weeks before the event. In another embodiment, the compound of the present invention is administered to the subject 10 min, 20 min, 30 min, 40 min, 50 min, 1 hr, 2 hrs, 3 hrs, 6 hrs, 12 hrs, 18 hrs, 24 hrs, 36 hrs, 48 hrs, 72 hrs, 96 hrs, 1 week, or 2 weeks after the event.

In one embodiment, the methods of the present application may further comprise, before administering the compound of the present invention, identifying a subject at risk of being exposed to a bacterium which can be used as a biological weapon. The subject at a risk of being exposed to a bacterium which can be used as a biological weapon includes, but is not limited to, a subject travelling to, entering, or being in a conflict region (e.g., a battlefield and combat zone), such as military personnel, intelligence personnel, and animals used in the military, a subject engaged or about to be engaged in a security operation, such as governmental authorities (e.g., police, governmental investigators, and secret service members) and other personnel (e.g., doctors, nurses, and rescue workers), and animals used in such an operation, and a subject in an geographical area that is likely to be a target of a terrorist attack (e.g., a metropolitan area, a city, an area where there is a large population (e.g., above 100,000, above 200,000, above 500,000, above 1 million, above 2 million, above 5 million, and above 10 million), and a location or area a damage to which is likely to cause a threat to national security or public health (e.g., a nuclear power plant, a chemical plant, an airport, and a hospital).

"Expose", "exposure", or "exposed" means that a subject comes in contact in any way with a bacterium or any component thereof (e.g., bacterial cell wall, bacterial cell membrane, a bacterial nucleic acid, a bacterial polynucleotide, a bacterial protein, a bacterial polypeptide, a bacterial spore, and a bacterial toxin). For example, a subject may be exposed to a bacterium or any component thereof by ingesting, inhaling, or touching anything which contains the bacterium or any component thereof. For example, the component of the bacterium is capable of causing an infection or symptoms of an infection in the subject. For example, the bacterial component is a bacterial spore.

In one embodiment, the invention pertains to a method of treating a bacterial infection in a subject, wherein the subject is exposed or suspected of being exposed to a bacterium or a component thereof, comprising administering to the subject an effective amount of Compound A' or Compound A, or a salt thereof. In another embodiment, the invention also pertains to a method of treating a bacterial infection in a subject, wherein the subject is exposed or suspected of being exposed to a bacterium or a component thereof, comprising administering to the subject Compound A' or Compound A, or a salt thereof, at a dose of about 10 mg to about 1000 mg. In one embodiment, the invention also pertains to a method of preventing a bacterial infection in a subject, wherein the subject is at a risk of being exposed to a bacterium or a component thereof, comprising administering to the subject an effective amount of a compound of Compound A' or Compound A, or a salt thereof. In another embodiment, the invention also pertains to a method of preventing a bacterial infection in a subject, wherein the subject is at a risk of being exposed to a bacterium or a component thereof, comprising administering to the subject an effective amount of Compound A' or Compound A, or a salt thereof, at a dose of about 10 mg to about 1000 mg. In one embodiment, the bacterium or a component thereof is formulated as an aerosol or power. In one embodiment, the bacterial component is a bacterial spore.

A compound of the invention, e.g., Compound A, may be administered to a subject by any mode of administration that can achieve a level of Compound A in the subject that is effective to treat or prevent an infection. In one embodiment, a compound of the present invention is administered orally. In another embodiment, a compound of the present invention is administered intravenously. In another embodiment, a compound of the present invention is administered intraperitoneally. In yet another embodiment, a compound of the present invention is administered subcutaneously.

In some embodiments, the compound of the invention may be administered at a dose of 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 12 mg/kg, 14 mg/kg, 16 mg/kg, 18 mg/kg, 20 mg/kg, 22 mg/kg, 24 mg/kg, 26 mg/kg, 28 mg/kg, 30 mg/kg, 32 mg/kg, 34 mg/kg, 36 mg/kg, 38 mg/kg, 40 mg/kg, 42 mg/kg, 44 mg/kg, 46 mg/kg, 48 mg/kg, 50 mg/kg, 52 mg/kg, 54 mg/kg, 56 mg/kg, 58 mg/kg, 60 mg/kg, 62 mg/kg, 64 mg/kg, 66 mg/kg, 68 mg/kg, 70 mg/kg, 72 mg/kg, 74 mg/kg, 76 mg/kg, 78 mg/kg, 80 mg/kg, 82 mg/kg, 84 mg/kg, 86 mg/kg, 88 mg/kg, 90 mg/kg, 92 mg/kg, 94 mg/kg, 96 mg/kg, 98 mg/kg, 100 mg/kg, 110 mg/kg, 120 mg/kg, 130 mg/kg, 140 mg/kg, 150 mg/kg, 160 mg/kg, 170 mg/kg, 180 mg/kg, 190 mg/kg or 200 mg/kg.

It should be understood that dose ranges comprising the above listed doses are also included in the present invention. For example, any of the above doses may be a lower part or an upper part of a dose range that is included in the present invention. Even further, it should be understood that all lists or collections of numerical values used throughout the present application also are intended to include ranges of the numerical values wherein any of the listed numerical values can be the lower part or upper part of a range. These ranges are intended to be included in the present invention.

In some embodiments, a compound of the invention, e.g., Compound A' or Compound A, may be administered at a dose of from about 10 to about 1000 mg, about 20 to about 750 mg, about 50 to about 500 mg, about 75 to about 400 mg, about 100 to about 300 mg, about 110 to about 290 mg, about 120 to about 280 mg, about 130 to about 270 mg, about 140 to about 260 mg, about 150 to about 250 mg, about 160 to about 240 mg, about 170 mg to about 230 mg, about 180 mg to about 220 mg, about 190 mg to about 210 mg, or about 200 mg. In another embodiment, the compound of the present invention, e.g., Compound A' or compound A, may be administered intravenously at a dose of about 5 to about 500 mg, about 10 to about 400 mg, about 25 to about 300 mg, about 50 to about 200 mg, about 50 to about 150 mg, about 60 to about 140 mg, about 70 mg to about 130 mg, about 80 mg to about 120 mg, about 90 mg to about 110 mg, or about 100 mg. In one embodiment, the compound of the invention, e.g., Compound A' or Compound A, may be administered orally at a dose of from about 5 to about 800 mg, about 10 to about 700 mg, about 25 to about 600 mg, about 50 to about 500 mg, about 100 to about 400 mg, about 150 to about 350 mg, about 200 mg to about 340 mg, about 250 mg to about 330 mg, about 270 mg to about 320 mg, about 280 to about 310, or about 300 mg.

In an embodiment, the compound of the invention, e.g., Compound A' or Compound A, may be administered intravenously at the dose of about 100 mg, about 200 mg, or about 300 mg. In another embodiment, the compound of the invention, e.g., Compound A' or Compound A, may be administered orally at the dose of about 300 mg, about 600 mg, or about 900 mg.

In one embodiment, an oral dose of compound of the invention, e.g., Compound A' or Compound A is 3 times larger than an intravenous dose of the compound of the invention, e.g., Compound A' or Compound A.

It will be understood that for all listed embodiments the dose of the compound of the invention, e.g., Compound A' or Compound A, is also an effective amount of the compound of the invention, e.g., Compound A' or Compound A.

In one embodiment, the effective amount of a compound of the present invention, e.g., Compound A or Compound A', when administered orally, is from about 10 to about 1000 mg, about 20 to about 750 mg, about 50 to about 500 mg, about 75 to about 400 mg, about 100 to about 300 mg, about 110 to about 290 mg, about 120 to about 280 mg, about 130 to about 270 mg, about 140 to about 260 mg, about 150 to about 250 mg, about 160 to about 240 mg, about 170 mg to about 230 mg, about 180 mg to about 220 mg, about 190 mg to about 210 mg, or about 200 mg. In another embodiment, the effective amount of a compound of the present invention, e.g., Compound A or compound A', when administered intravenously, is from about 5 to about 500 mg, about 10 to about 400 mg, about 25 to about 300 mg, about 50 to about 200 mg, about 50 to about 150 mg, about 60 to about 140 mg, about 70 mg to about 130 mg, about 80 mg to about 120 mg, about 90 mg to about 110 mg, or about 100 mg.

In one embodiment, a salt of a compound of the present invention is a hydrochloride salt. In another embodiment, a salt of a compound of the present invention is a tosylate salt. In a further embodiment, a compound of the present invention is administered orally as a free base or as a tosylate salt. In another embodiment, a compound of the present invention is administered intravenously as the hydrochloride salt. In yet another embodiment, a compound of the present invention is a mixed salt, e.g., mixed hydrochloride and tosylate salt.

In another embodiment, a compound of the present invention, e.g., Compound A or Compound A', may be administered once per day, either intravenously or orally.

In some embodiments, a compound of the present invention, e.g., Compound A or Compound A', may be administered for at least 3 days, at least 7 days, at least 14 days, at least 21 days, at least 30 days or at least 60 days. For example, the administration of the compound of the present invention may last for 3 days to 7 days, for 3 days to 14 days, for 3 days to 21 days, for 3 days to 30 days, for 3 days to 60 days, for 7 days to 14 days, for 7 days to 21 days, for 7 days to 30 days, for 7 days to 60 days, for 14 days to 21 days, for 14 days to 30 days, for 14 days to 60 days, for 21 days to 30 days, for 21 days to 60 days, or for 30 days to 60 days.

For example, a compound of the present invention, e.g., Compound A or Compound A', may be administered for 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days, 51 days, 52 days, 53 days, 54 days, 55 days, 56 days, 57 days, 58 days, 59 days or 60 days.

In some embodiments, the method comprises administering to the subject one or more loading doses of the compound, followed by one or more maintenance doses of the compound. In one embodiment, the one or more loading dose may be greater than the one or more maintenance dose.

In some embodiments, administration of a compound of the present invention, e.g., Compound A or Compound A', to a subject may comprise administering one or more loading doses of the compound, followed by one or more maintenance doses of the compound. In some embodiments, the one or more loading dose of the compound may be greater than the one or more maintenance dose of the compound. For example, the loading dose may be about 200 mg, while the maintenance dose may be about 150 mg, 100 mg or 50 mg; or the loading dose may be about 400 mg, while the maintenance dose may be about 300 mg, 250 mg, 200 mg, 150 mg, 100 mg or 50 mg; or the loading dose may be about 100 mg, while the maintenance dose may be about 75 mg, about 50 mg or about 25 mg.

The loading dose of the compound of the invention and the maintenance dose of the compound of the invention may be administered via same routes or different routes. For example, the loading dose may be administered intravenously and the maintenance dose may be administered orally. In other embodiments, both the loading dose and the maintenance dose may be administered orally, or the loading dose and the maintenance dose may be administered intravenously.

In some embodiments, the loading dose of the compound of the invention, e.g., Compound A' or Compound A, may be an oral dose or an intravenous dose administered twice daily, and the maintenance dose may be an oral dose or an intravenous dose administered once daily. For example, the compound of the invention, e.g., Compound A' or Compound A, may be administered as an intravenous loading dose of 100 mg twice daily, followed by an intravenous maintenance dose of 100 mg once daily. In another example, the compound of the invention, e.g., Compound A' or Compound A, may be administered as an intravenous loading dose of 100 mg twice daily, followed by an oral maintenance dose of 300 mg once daily. In yet another example, the compound of the invention, e.g., Compound A' or Compound A, may be administered as an oral loading dose of 300 mg twice daily, followed by an oral maintenance dose of 300 mg once daily.

The term "treating" or "treatment" refers to the amelioration or diminishment of one or more symptoms of the disorder, e.g., a bacterial infection, to be treated.

The term "prophylaxis", "prevent", or "prevention" means to prevent or reduce the risk of a bacterial infection.

A bacterium is "easily produced or disseminated" if the bacterium can be produced or disseminated by routine methods, processes, or techniques and with common materials, reagents, equipment, etc. available in the art, or by methods, processes, or techniques and with materials, reagents, equipment, etc. which are accessible to and can be operated or used by a lay person having little or no training in the art.

The term "moderate morbidity" refers to morbidity of no less than 10%, no less than 15%, no less than 20%, no less than 25%, no less than 30%, no less than 35%, no less than 40%, or no less than 45%. The term "high morbidity" refers to morbidity of no less than 50%, no less than 55%, no less than 60%, no less than 65%, no less than 70%, no less than 75%, no less than 80%, no less than 85%, no less than 90%, or no less than 95%.

The term "moderate mortality" refers to mortality of no less than 10%, no less than 15%, no less than 20%, no less than 25%, no less than 30%, no less than 35%, no less than 40%, or no less than 45%. The term "high mortality" refers to mortality of no less than 50%, no less than 55%, no less than 60%, no less than 65%, no less than 70%, no less than 75%, no less than 80%, no less than 85%, no less than 90%, or no less than 95%.

The term "resistance" or "resistant" refers to the antibiotic/organism standards as defined by the Clinical and Laboratories Standards Institute (CLSI) and/or the Food and Drug Administration (FDA).

The term "subject" includes animals which are subject to a bacterial infection. Examples of subjects include animals such as farm animals (e.g., cows, pigs, horses, goats, rabbits, sheep, chickens, etc.), lab animals (mice, rats, monkeys, chimpanzees, etc.), pets (e.g., dogs, cats, ferrets, hamsters, etc.), birds (e.g., chickens, turkeys, ducks, geese, crows, ravens, sparrows, etc.), primates (e.g., monkeys, gorillas, chimpanzees, bonobos, and humans), and other animals (e.g., squirrels, raccoons, mice, rats, etc.). In one embodiment, the subject is a mouse or rat. In one embodiment, the subject is a cow, a pig, or a chicken. In one embodiment, the subject is a human.

The compounds of the present invention may be administered by any route which allows the compounds to perform its intended function, e.g., treat or prevent a bacterial infection. Examples of routes include orally, intravenously, and topically. In one embodiment, a compound of the present invention is administered orally. In another embodiment, a compound of the present invention is administered intravenously.

The term "effective amount" includes the amount of a compound of the present invention needed to treat or prevent a bacterial infection. For example, an effective amount describes an efficacious level sufficient to achieve the desired therapeutic effect through the killing of bacteria and/or inhibition of bacterial growth. In one embodiment, the effective amount is sufficient to eradicate the bacterium or bacteria causing the infection. In some embodiments, the effective amount is the dose of the compound of the invention, e.g., Compound A' or Compound A, that is administered to the subject, e.g., orally or intravenously.

The term "about" refers to a range of values which can be 15%, 10%, 8%, 5%, 3%, 2%, 1%, or 0.5% more or less than the specified value. For example, "about 10%" can be from 8.5% to 11.5%. In one embodiment, the term "about" refers to a range of values which are 5% more or less than the specified value. In another embodiment, the term "about" refers to a range of values which are 2% more or less than the specified value. In another embodiment, the term "about" refers to a range of values which are 1% more or less than the specified value.

The structures of the compounds of the present invention may include double bonds or asymmetric carbon atoms.

Such compounds can occur as racemates, racemic mixtures, single enantiomers, individual diastereomers, diastereomeric mixtures, and cis- or trans- or E- or Z-double bond isomeric forms. Such isomers can be obtained in substantially pure form by classical separation techniques and by stereochemically controlled synthesis. Furthermore, the structures and other compounds and moieties discussed in the present invention also include all tautomers thereof.

The compounds of the present invention may be basic or acidic, and are capable of forming a wide variety of salts with various acids or bases. The acids that may be used to prepare pharmaceutically acceptable salts of the compounds of the present invention that are basic are those that form non-toxic acid addition salts, such as HCl salt, HBr salt, HI salt, nitrate, sulfate, bisulfate, phosphate, acid phosphate, isonicotinate, acetate, lactate, salicylate, citrate, acid citrate, tartrate, bitartrate, pantothenate, ascorbate, succinate, maleate, gentisinate, fumarate, gluconate, glucaronate, saccharate, formate, benzoate, glutamate, methane sulfonate, ethanesulfonate, benzene sulfonate, p-toluenesulfonate (i.e., tosylate) and palmoate. The bases that may be used to prepare pharmaceutically acceptable salts of the compounds of the present invention that are acidic are those that form a non-toxic base salts, such as those salts containing alkali metal cations (e.g., $Na^+$ and $K^+$), alkaline earth metal cations (e.g., $Mg^{++}$ and $Ca^{++}$), and amines The compounds of the present invention that are basic in nature are capable of forming a wide variety of salts with various inorganic and organic acids. The acids that may be used to prepare pharmaceutically acceptable acid addition salts of the compounds of the present invention that are basic in nature are those that form nontoxic acid addition salts, i.e., salts containing pharmaceutically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate (i.e., tosylate), and palmoate (i.e., 1,1'-methylene-bis-(2 hydroxy-3-naphthoate)) salts. Although such salts must be pharmaceutically acceptable for administration to a subject, e.g., an animal, it is often desirable in practice to initially isolate the compounds of the present invention from the reaction mixture as pharmaceutically unacceptable salts and then simply convert the latter back to the free base compounds by treatment with an alkaline reagent and subsequently convert the latter free base to pharmaceutically acceptable acid addition salts. The acid addition salts of the compounds of the present invention are readily prepared by treating the compounds with a substantially equivalent amount of the chosen mineral or organic acid in an aqueous solvent medium or in a suitable organic solvent, such as methanol or ethanol. Upon careful evaporation of the solvent, the desired solid salts are readily obtained.

In one embodiment, a salt of a compound of the present invention is a hydrochloride salt. In another embodiment, a salt of a compound of the present invention is a tosylate salt. In a further embodiment, a compound of the present invention is administered orally as a free base or as a tosylate salt. In another embodiment, a compound of the present invention is administered intravenously as the hydrochloride salt. In yet another embodiment, a compound of the present invention is a mixed salt, e.g., mixed hydrochloride and tosylate salt.

It is to be understood that wherever values and ranges are provided herein, e.g., in ages of subject populations, dosages, and time durations, etc., all values and ranges encompassed by these values and ranges, are meant to be encompassed within the scope of the present invention. Moreover, all values in these values and ranges may also be the upper or lower limits of a range.

The compounds of the present invention can be synthesized by using art recognized techniques, such as those described in U.S. Pat. Nos. 6,846,939 and 7,553,828, and US Patent Publication No. 20080287401, the contents of each of which are incorporated herein by reference in their entirety. The compounds thus obtained can be further purified, for example, by flash column chromatography, high performance liquid chromatography, crystallization, or any known purification method.

In one embodiment, the compounds of the present invention can be synthesized according to the synthetic scheme as shown below and as described in US 20080287401:

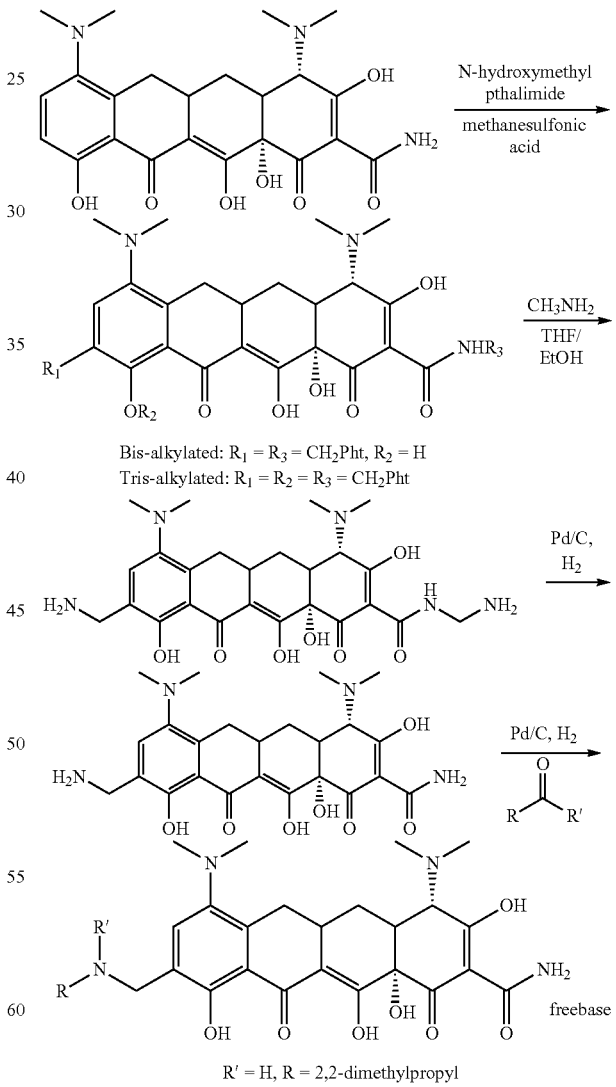

In one embodiment, the compounds of the present invention can be purified by chromatography, which comprises injecting an aqueous low pH solution of the compound into an HPLC in a polar organic solvent gradient, and combining the product fractions. Selection of suitable acidic mobile phases enhances process stability and selectivity. Organic and mineral acid mobile phases are effective at separating by-products, including epimer impurities, and closely-eluting by products through pH control or choice of acid. Acidic mobile phases also protect against oxidative degradation of the compound. For example, the low pH solution has a pH of about 2-3. Examples of solutions that can used include 0.1% aqueous solutions of methane sulfonic acid and 0.1% aqueous solutions of trifluoroacetic acid. An isocratic gradient of 94% of the aqueous solution and 6% acetonitrile or another polar organic solvent may be used to purify the compound from epimeric and closely eluting by-products. The resulting aqueous product fractions can be combined, and the pH may be adjusted to about 4.0-4.5 using a base (e.g., NaOH). Hydrophobic impurities and oxidative degradents of the compound may be removed by washing the aqueous solution with a non-polar organic solvent (e.g., $CH_2Cl_2$). The organic layers may be discarded and the aqueous layers may be combined and retained. It should be noted that the organic solvents, such as methylene chloride, may be used to selectively remove late-eluting hydrophobic impurities such as 4-carbonyl by-products and other oxidative degradents from the acidic aqueous solution of the compound. The pH of the combined aqueous layers was adjusted to neutral pH (e.g., about 7.5 to about 8.5). The pH may be adjusted by the addition of a base, such as NaOH. The neutral solution may then be washed with a non-polar organic solvent, such as methylene chloride. It should be noted that selective pH adjustment to neutral pH ranges may also allow the compound to be extracted into the organic solvent while retaining undesired β-epimer and by-products in the aqueous phase.

The reagents that may be used in the synthetic routes described in the above patents may include, for example, solvents, reagents, catalysts, and protecting group and deprotecting group reagents. The synthetic routes may also include additional steps, either before or after the steps described specifically therein, to add or remove suitable protecting groups in order to ultimately allow synthesis of the desired tetracycline compounds. In addition, various synthetic steps may be performed in an alternate sequence or order to give the desired compounds. For example, compounds may be further modified via conventional chemical transformations to produce the compounds of the present invention. Synthetic chemistry transformations and protecting group methodologies (protection and deprotection) are known in the art and include, e.g., those described in R. Larock, Comprehensive Organic Transformations, VCH Publishers (1989); T. W.
Greene and P. G. M. Wuts, Protective Groups in Organic Synthesis, 3rd Ed., John Wiley and Sons (1999); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995).

The synthetic routes described in the above patents are used only for illustrative purposes. One skilled in the art, in view of the schemes and the examples provided therein, would appreciate that all of the compounds of the present invention can be made by similar methods that are well known in the art.

The efficacy of the compound of the present invention in treating or preventing a bacterial infection may be assessed by using common methods known in the art. In one embodiment, the efficacy may be determined by Minimum Inhibition Concentration (MIC) assay. For example, the compound of the present invention is serially diluted and then added to the growth medium, e.g., cation-adjusted Mueller Hinton broth (CAMHB) of the bacterial culture. The lowest concentration of the compound of the present invention that inhibits 50% or 90% bacterial growth (i.e., $MIC_{50}$ or $MIC_{90}$) is determined and, if necessary, compared with $MIC_{50}$ or $MIC_{90}$ of other antibiotics. In another embodiment, the efficacy may be determined through in vivo assays known in the art (e.g., animal experiments). For example, the compound of the present invention is administered to experimental animals (e.g., mice and rats) at decreasing amounts. The lowest amount of the compound of the present invention that treats the experimental animal (e.g., ameliorates symptoms of a bacterial infection, prolongs the survival time of the animal, and allows animal to survive the bacterial infection) or prevents the experimental animals from being infected by the bacterium or developing any symptoms of the infection is determined and, if necessary, compared with the lowest amount of other antibiotics which achieves the same results.

The invention also pertains to pharmaceutical compositions comprising a therapeutically effective amount of a compound of the present invention (e.g., Compound A) or a salt thereof and, optionally, a pharmaceutically acceptable carrier. In a further embodiment, the invention pertains to a pharmaceutical composition comprising from about 10 to about 1000 mg of a compound of the present invention (e.g., Compound A or Compound A') or a salt thereof and a pharmaceutically acceptable carrier. In a further embodiment, the pharmaceutically acceptable carrier is acceptable for oral administration. In another further embodiment, a compound of the present invention is a free base or a tosylate salt.

In yet another further embodiment, the composition comprises from about 20 to about 750 mg, about 50 to about 500 mg, about 75 to about 400 mg, about 100 to about 300 mg, about 110 to about 290 mg, about 120 to about 280 mg, about 130 to about 270 mg, about 140 to about 260 mg, about 20 about 150 to about 250 mg, about 160 to about 240 mg, about 170 mg to about 230 mg, about 180 mg to about 220 mg, about 190 mg to about 210 mg, or about 200 mg of a compound of the present invention (e.g., Compound A or Compound A') or a salt thereof.

In another embodiment, the invention also pertains to a pharmaceutical composition comprising from about 5 to about 500 mg of a compound of the present invention (e.g., Compound A or Compound A') or a salt thereof and a pharmaceutically acceptable carrier suitable for intravenous administration. In yet another further embodiment, the composition comprises from about 10 to about 400 mg, about 25 to about 300 mg, about 50 to about 200 mg, about 50 to about 150 mg, about 60 to about 140 mg, about 70 mg to about 130 mg, about 80 mg to about 120 mg, about 90 mg to about 110 mg, or about 100 mg of a compound of the present invention (e.g., Compound A or Compound A') or a salt thereof.

The language "pharmaceutically acceptable carrier" includes substances capable of being co-administered with a compound of the present invention (e.g., Compound A or Compound A'), and which allow the compound to perform its intended function, e.g., treat or prevent a bacterial infection. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid mono glycerides and diglycerides, petroethral fatty acid esters, hydroxymethyl cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the compounds of the present invention.

The compounds of the present invention and pharmaceutically acceptable salts thereof can be administered via either the oral, parenteral or topical routes. In general, these compounds are most desirably administered in effective dosages, depending upon the weight and condition of the subject being treated and the particular route of administration chosen. Variations may occur depending upon the species of the subject being treated and its individual response to the medicament, as well as on the type of pharmaceutical formulation chosen and the time period and interval at which such administration is carried out.

The compounds and pharmaceutical compositions of the present invention may be administered alone or in combination with other known compositions for treating tetracycline responsive states in a subject. The language "in combination with" a known composition is intended to include simultaneous administration of the composition of the present invention and the known composition, administration of the composition of the present invention first, followed by the known composition, and administration of the known composition first, followed by the composition of the present invention. Any of the therapeutically composition known in the art for treating tetracycline responsive states can be used in the methods of the present invention.

The compounds and pharmaceutical compositions of the present invention may be administered alone or in combination with pharmaceutically acceptable carriers or diluents by any of the routes previously mentioned, and the administration may be carried out in single or multiple doses. For example, the compounds of the present invention can be administered advantageously in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of the present invention are present in such dosage forms at concentration levels ranging from about 5.0% to about 70% by weight.

For oral administration, tablets containing various excipients such as microcrystalline cellulose, sodium citrate, calcium carbonate, dicalcium phosphate, and glycine may be employed along with various disintegrants such as starch (and preferably corn, potato or tapioca starch), alginic acid, and certain complex silicates, together with granulation binders like polyvinylpyrrolidone, sucrose, gelatin, and acacia. Additionally, lubricating agents such as magnesium stearate, sodium lauryl sulfate, and talc are often very useful for tabletting purposes. Solid compositions of a similar type may also be employed as fillers in gelatin capsules; preferred materials in this connection also include lactose or milk sugar as well as high molecular weight polyethylene glycols.

When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin, and various like combinations thereof.

For parenteral administration (including intraperitoneal, subcutaneous, intravenous, intradermal, or intramuscular injection), solutions of the compounds of the present invention in either sesame or peanut oil or in aqueous propylene glycol may be employed. The aqueous solutions should be suitably buffered if necessary and the liquid diluent first rendered isotonic. These aqueous solutions are suitable for intravenous injection purposes. The oily solutions are suitable for intra-articular, intramuscular and subcutaneous injection purposes. The preparation of all these solutions under sterile conditions is readily accomplished by standard pharmaceutical techniques well known to those skilled in the art. For parenteral application, examples of suitable preparations include solutions, preferably oily or aqueous solutions as well as suspensions, emulsions, or implants, including suppositories. Therapeutic compounds may be formulated in sterile form in multiple or single dose formats such as being dispersed in a fluid carrier such as sterile physiological saline or 5% saline dextrose solutions commonly used with injectables.

For enteral application, particularly suitable are tablets, dragees, or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

EXEMPLIFICATION OF THE INVENTION

Example 1

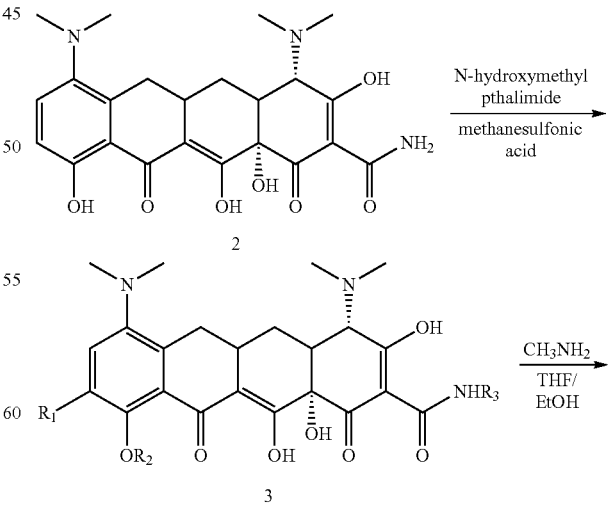

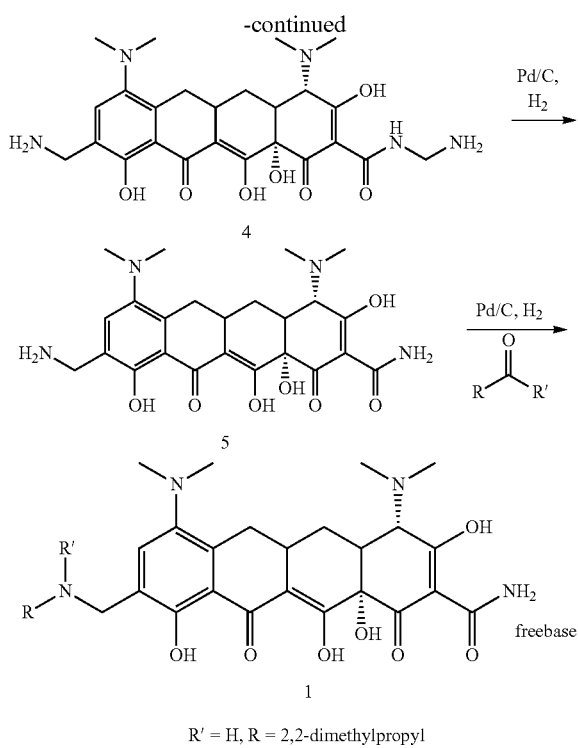

R' = H, R = 2,2-dimethylpropyl

Minocycline hydrochloride was dissolved in methylsulfonic acid or hydrofluoric acid with methyl sulfonic anhydride. N-hydroxymethyl phthalimide was added to the reaction mixture. The mixture was stirred at 20-35° C. until the reaction was complete. The acid solution was added to an ice/water mixture and the triflic salt was readily precipitated, filtered and collected. The salt was re-dissolved in acetone and brought to a neutral pH with base. The product was precipitated by the addition of water. The product was isolated as a mixture of the bis and tris alkylated product. The isolated material of this reaction was enriched in the desired bis ratio (90%).

The solid was suspended in the EtOH Aminolysis was carried out by using methylamine A phthalamide by-product precipitated as the reaction progressed and was removed by filtration. The light yellow solid product was precipitated out by the addition of about 1.5 volumes of t-butylmethylether to the reaction mixture, and collected through a simple filtration that left many small impurities and methylamine reagent in the solution. Further purification of the compound was performed through re-slurrying with methanol.

Compound 4 as freebase was transferred to a hydrogenation vessel which was charged with methanol and aldehyde. An inactivated Pd/C catalyst was charged and the vessel was pressurized with hydrogen gas. The reaction mixture was hydrogenated under hydrogen pressure around 30 Psi for about 24 hours. When conversion of compound 4 to 1 was complete, the solution was filtered and washed through a Celite pad. At this point the reaction mixture contained very low β C-4 epimer, around 3-7%.

The product (1) was worked up and isolated selectively from its impurities. The pH of the solution was adjusted to about 4.5 with concentrated HCl and the solution was washed with dichloromethane. Sulfites were added to the aqueous layer and the product was extracted with dichloromethane at pH of about 7 to 8 to selectively recover the preferred epimer product (e.g., a). The dichloromethane layers were combined and concentrated, and 2L of n-heptane was added to precipitate the product. Further purification was obtained by repeating the work-up procedure with or without t-butylmethylether to dissolve the crude product.

9-(2',2'-dimethylpropyl aminomethyl)-minocycline dihydrochloride (200 mg, 1 eq.), DMF and trimethylacetaldehyde (45 μL, 1 eq.) were combined in 40 mL flasks and stirred. Triethylamine (150 μL, 3 eq.) was then added. After stirring at room temperature for several minutes, NaBH(OAc)$_3$ (175 mg, 2 eq.) and InCl$_3$ (9 mg, 0.1 eq.) was added. After one hour, the reaction was clear and red. The reaction was quenched with methanol, the solvent was removed, and Compound A was obtained.

Example 2

Crude 9-(2',2'-dimethylpropyl aminomethyl) minocycline freebase (40 g) was dissolved in 150 mL of buffer A (0.1% aqueous solution of methane sulfonic acid—MSA) and the pH was adjusted to 2-3 with MSA. The solution was filtered and injected into an HPLC and the product was eluted with an isocratic gradient of 94% buffer A and 6% acetonitrile. The product fraction collection was initiated when the product peak was detected. Each fraction was analyzed and an acceptance criterion of greater than 80% AUC of the main peak was used for the early product fractions. When combining fractions, the level of impurities and relative concentration of the pooled fractions was factored into the selection criteria that meet the final product specifications. To the product fractions was added a 10% aqueous solution of sodium sulfite equal to 10% of the original volume of the collected fractions.

A product fraction volume of 3.5 liters (including sodium sulfite) was collected and the pH was adjusted to 4.0-4.5 using a solution of sodium hydroxide. The aqueous solution was washed with 2 liters of dichloromethane and the organic layer was separated and discarded. The pH of the aqueous layer was adjusted to 7.5-8.5 using sodium hydroxide and the product was extracted four times with 2.4 liters of dichloromethane. The pH was readjusted to 7.5-8.5 with sodium hydroxide, prior to each extraction.

The four dichloromethane layers were combined and concentrated to about 200 ml, which was then added slowly (over a period of about 10 minutes) to a vigorously stirred n-heptane (2.5 L). The suspension was stirred for about 10 minutes at room temperature and diluted slowly (over a period of 5 minutes) with n-heptane 1.5 L. The slurry was cooled to 0-5° C. and stirred for 1-2 hours. The suspended solid was filtered and washed with 3×150 mL portions of n-heptane. The product was dried under vacuum at 40° C. for at least 24 hours until a constant weight was achieved and the levels of all residual solvents were within specification. Approximately 13.6 g of 9-(2',2'-dimethylpropyl aminomethyl) minocycline freebase was isolated as a yellow solid. The off-cuts were isolated in a similar manner and yielded 1.64 g.

Example 3

Bacterial inoculums were prepared by suspending into cation-adjusted Mueller-Hinton broth (CAMHB) colonies from 18-24 h B. anthracis, B. pseudomallei, or B. mallei plates, or 42-48 h F. tularensis or Y. pestis plates that were incubated at 35° C. Sheep Blood agar (SBA) plates were used for *B. anthracis* and *Y. pestis*, chocolate agar plates for *F. tularensis*, and Trypticase Soy agar (TSA) plates for *B. pseudomallei* and *B. mallei*. Suspended cultures were diluted with CAMHB to a bacterial cell density of $10^5$ CFU/mL adjusted based on $OD_{600}$. Conversion factors used for each pathogen were: *B. anthracis* ($3.82 \times 10^7$ CFU/mL/OD), *B. mallei* and *B. pseudomallei* ($5.0 \times 10^8$ CFU/mL/OD), *Y. pestis* ($5.34 \times 10^8$ CFU/mL/OD), and *F. tularensis* ($3.89 \times 10^{10}$ CFU/mL/OD). 50 µL of the adjusted dilution was added to each well of 96-well plates for a final inoculum of ~$5 \times 10^4$ CFU/well.

The inoculated 96-well plates were incubated at 35° C. Antibiotics were serially diluted two-fold in 50 µL of CAMHB and added to individual wells of the plates. For all steps with *F. tularensis*, CAMHB was supplemented with 2% Isovitalex (Becton Dickinson). The antibiotic ranges were 8-0.0039 ~µg/ml or 64-0.03125 µg/ml based on a final well volume of 100 µL after inoculation. MICs were determined by the microdilution method in the 96-well plates according to CLSI guidelines. MICs were determined visually at 18-24 h or 42-48 h (for *F. tularensis* and *Y. pestis*) and also by reading the plates at 600 nm (SpectroMax M2, Molecular Devices). Quality control of the antibiotic stocks was established by using *E. coli* ATCC 25922, *P. aeruginosa* ATCC 27853, and *S. aureus* ATCC 29213. Inoculums of these control bacteria were prepared as described above from 18-24 h SBA plates. Conversion factors were: *E. coli* ($6.83\times10^8$ CFU/mL/OD), *P. aeruginosa* ($5.74\times10^{10}$ CFU/mL/OD), and *S. aureus* ($2.07\times10^{10}$ CFU/mL/OD).

Stock solutions of Compound A at 5.15 mg/ml were made in 100% DMSO. Prior to use, the stock solution was diluted in CAMHB before being added to the 96-well plates as described above. Comparator antibiotics ciprofloxacin, ceftazidime, and azithromycin were all purchased from USP, made into 5.15 mg/ml stocks according to the CLSI M 100-S 18 Table 4 guidelines and stored at −70° C. until use.

Example 4

Compound A was highly active against strains of *Bacillus anthracia* and *B. mallei*, and also had significant activity against *Yersinia pestis* and *Franciscella tularensis*, demonstrating excellent $MIC_{50}$ and $MIC_{90}$ values against these target pathogens (Table 1). The MIC values for Compound A were comparable to those for doxycycline which is currently recommended for treatment of diseases caused by these pathogens. Unlike doxycycline, however, Compound A is expected to be active against strains possessing either efflux or ribosomal mechanisms of resistance.

TABLE 1

In Vitro Activity of Compound A

| | | | Historical Data | |
|---|---|---|---|---|
| | Compound A | Ciprofloxacin | Tetracycline | Doxycycline |
| *Y. pestis* | | | | |
| MIC range (μg/mL) | 0.125-2 | 0.0039-0.0625 | 0.25-2 | 0.0625-2 |
| $MIC_{50}$ | 1 | 0.01563 | 0.5 | 0.5 |
| $MIC_{90}$ | 1 | 0.03125 | 2 | 1 |
| *B. anthracis* | | | | |
| MIC range (μg/mL) | <0.03125-0.0625 | 0.03125-.25 | <0.03125-1 | 0.03125-0.0625 |
| $MIC_{50}$ | 0.03125 | 0.0625 | <0.03125 | 0.03125 |
| $MIC_{90}$ | 0.0625 | 0.125 | 0.125 | 0.0625 |
| *F. tularensis* | | | | |
| MIC range (μg/mL) | 0.5-2 | 0.0078-0.25 | <0.03125-1 | 0.03125 |
| $MIC_{50}$ | 1 | 0.0078 | 0.125 | 0.25 |
| $MIC_{90}$ | 2 | 0.01563 | 0.5 | 0.5 |
| *B. mallei* | | | | |
| MIC range (μg/mL) | <0.03125-0.5 | 0.0625-1 | 0.01563-0.5 | 0.015563-0.5 |
| $MIC_{50}$ | 0.125 | 0.5 | 0.125 | 0.0625 |
| $MIC_{90}$ | 0.25 | 1 | 0.25 | 0.125 |
| *B. pseudomallei* | | | | |
| MIC range (μg/mL) | 2->64 | 0.5-32 | 1->8 | 0.0625 |
| $MIC_{50}$ | 64 | 2 | 2 | 0.5 |
| $MIC_{90}$ | >64 | 4 | >8 | 8 |

Example 5

The in vitro activity of Compound A was assessed in independent laboratories using bacteria isolated from clinical specimens. For all aerobic or facultatively anaerobic organisms, MICs were determined by the broth microdilution method recommended by the Clinical & Laboratory Standards Institute (CLSI, M7-A7, 2006) using cation adjusted Mueller-Hinton Broth (CAMHB, DIFCO Lot #5230237). When testing fastidious organisms such as streptococci, the CAMHB was supplemented with 3-5% lysed horse blood (Hemostat Lot # H06036). Haemophilus Test Medium (HTM) was used for testing *Haemophilus influenzae*. A selected group of microorganisms was also tested by agar dilution using the methods specified by CLSI document M7-A7, 2006 using plain Mueller-Hinton Agar (Difco Lots 1303004 & 5011641) for testing the majority of the isolates or supplemented with 5% sheep blood (Hema Resource Lot

1127-100140-04) for testing the streptococci. All broth media used was less than 12 hours old at the time of MIC tray production.

All anaerobic strains were tested by broth microdilution and agar dilution using the methods specified by the CLSI (M11-A6, 2004). Brucella broth (BBL Lot #5227153), supplemented with 5 µg/ml of hemin (Sigma Lot #89K0914), 1 µg/ml of vitamin K1 (Sigma Lot #120K1413) and 5% lysed horse blood (Hemostat Lot # H06036) was used for testing all anaerobic strains. In addition, all strains were tested using the agar dilution method using Brucella agar (BBL Lot #6160970) supplemented with 5 µg/ml of hemin, 1 µg/ml of vitamin K1 and 5% lysed sheep blood (Hema Resource Lot #1127-100140-04). Fresh broth less than 12 hours old was used for preparing MIC trays. The agar dilution plates were poured on the same day as testing.

Compound A exhibited activity against almost all of the clinical isolates tested (Table 2). This included isolates that were resistant to current tetracyclines such as doxycycline (Table 2). Compound A was also active against pathogens expected to be encountered in ABSSSI and CABP irrespective of resistance to commonly used antibiotics, including tetracycline. The in vitro activity of Compound A was not affected by serum or lung surfactant, important characteristics consistent with potential utility in infections involving the lower respiratory tract.

TABLE 2

Activity of Compound A versus Doxycycline Against Bacterial Pathogens

| | | | Compound A/Doxycycline | |
|---|---|---|---|---|
| Class | Species | #Isolates | $MIC_{50}$ (µg/mL) | $MIC_{90}$ (µg/mL) |
| Gram-positive pathogens[b] | Staphylococcus aureus (MSSA) | 52 | 0.25/0.12 | 0.25/0.25 |
| | Staphylococcus aureus (MRSA) | 111 | 0.25/0.12 | 0.25/2 |
| | Coagulase-negative staphylococci | 152 | 0.25/0.25 | 1/2 |
| | Enterococcus faecalis (VSE) | 107 | 0.25/8 | 0.5/8 |
| | Enterococcus facecalis (VRE) | 47 | 0.12/0.25 | 0.25/8 |
| | Enterococcus faecium (VSE) | 56 | 0.12/0.12 | 0.12/16 |
| | Enterococcus faecium (VRE) | 100 | 0.12/8 | 0.12/8 |
| | Streptococcus pneumonia | 104 | 0.12/0.25 | 0.12/8 |
| | Streptococcus pneumoniae (PRSP) | 51 | 0.12/8 | 0.12/8 |
| | Streptococcus pyogenes | 104 | 0.12/25 | 0.12/0.25 |
| | Streptococcus agalactiae | 53 | 0.25/8 | 0.25/16 |
| Gram-negative pathogens[b] | Haemophilus influenza | 105 | 0.5/0.5 | 1/1 |
| | Moraxella catarrhalis | 105 | 0.25/0.25 | 0.25/0.25 |
| | Escherichia coli | 203 | 2/8 | 4/>32 |
| | Enterobacter aerogenes | 51 | 2/2 | 4/4 |
| | Enterobacter cloacae | 62 | 2/4 | 16/16 |
| | Klebsiella pneumonia | 204 | 2/2 | 8/>32 |
| | Proteus mirabilis | 11 | 16/16 | 32/>32 |
| | Salmonella spp. | 52 | 2/4 | 8/32 |
| | Shigella spp. | 51 | 1/1 | 2/32 |
| | Pseudomonas aeruginosa | 22 | 32/32 | 64/32 |
| | Acinetobacter baumannii | 53 | 0.25/0.25 | 4/2 |
| | Burkholderia cepacia | 29 | 2/4 | 64/>32 |
| Anaerobic pathogens[b] | Bacteroides fragilis | 100 | 1/8 | 4/16 |
| | Clostridium difficile | 27 | 0.12/0.03 | 0.12/1 |
| | Clostridium perfringens | 100 | 1/2 | 4/8 |
| Atypical pathogens | Legionella pneumophila | 25 | 0.25/1 | 0.25/1 |
| | Chlamydia pneumonia | 3 | 0.25/ND[a] | 0.25/ND |

[a]ND—Not Tested.

[b]MICs determined by broth microdilution using fresh media. Data from Brown, S., and M. M. Traczewski, 2007. MK-2764: In vitro Spectrum of Activity, Confirmation of Disk Mass, Agar Dilution Validation and Short Term Stability using Fresh Media. The Clinical Microbiology Institute Report, Wilsonville, OR.

Example 6

The in vivo activity of Compound A was demonstrated in multiple animal models of infection using various pathogens. As shown in Table 3, Compound A was generally as potent or more potent and as effective or more effective than, minocycline, vancomycin, and linezolid.

TABLE 3

Animal Models of Infection

| Infecting bacterial species | Animal | Type of Infection | $PD_{50}^a/ED_{50}^b$ (mg/kg) |
|---|---|---|---|
| S. pneumoniae | Mice | acute systemic | 0.09-0.14 |
| | Mice | pulmonary | 7.4 |
| | Mice (neutropenic) | pulmonary | 11-27.1 |
| | Mice (neutropenic) | thigh wound | 0.14-0.75 |
| S. aureus | Mice | acute systemic | 0.4 |
| | Mice (neutropenic) | thigh wound | 5.9 |
| E. faecalis | Mice | renal infection | 4.5 |
| H. influenza | Mice | pulmonary | 4.7 |
| E. coli | Mice | urinary tract | 4.3 |

$^a PD_{50}$ (Protective Dose, 50%) defined as the dose required to achieve 50% survival.
$^b ED_{50}$ (Effective Dose, 50%) defined as the dose required to achieve a 2 log10 reduction in bacterial burden (cfu/g) at the target organ compared to untreated controls.

Example 7

The in vivo activity of Compound A (omadacycline) was tested in lethal *Y. pestis* post exposure prophylactic (PEP) infection model. BALB/c 6-8 week old female mice were infected by 29.9 $LD_{50}$s of *Y. pestis* (C092) via whole body aerosol. Ten mice per each group were used. Compound A was administered intraperitoneally twenty-five hours post-infection at the doses of 5, 10, 20 and 40 mg/kg every 12 hours for 7 days. Doxycycline at the doses of 5, 10, 20 and 40 mg/kg and ciprofloxacin at the dose of 15 mg/kg were used as positive controls. Mice were followed for 14 days post-infection, and percent survival was determined.

The results are presented in FIGS. 1 which demonstrates that Compound A at 40 mg/kg is more effective as doxycycline at 40 mg/kg and is at least as effective or ciprofloxacin at 15 mg/kg at treating *Y. pestis* infection for at least 14 days post-infection. In this experiment, MIC for Compound A was 1 μg/mL, for doxycycline was 0.5 μg/mL, and for ciprofloxacin is 0.06 μg/mL. Also, $PD_{50}$ for Compound A was 23.5 (range of 20.1 to 27.0 mg/kg), while $PD_{50}$ for doxycycline was 29.7 (range of 20.7 to 38.8).

Example 8

The in vivo activity of Compound A (omadacycline) was tested in lethal *B. anthracis* post exposure prophylactic (PEP) infection model. BALB/c 6-8 week old female mice were infected by 30.5 $LD_{50}$s of *B. anthracis* AMES strain via whole body aerosol. Ten mice per each group were used. Compound A was administered intraperitoneally twenty-four hours post-infection at the doses of 0.75, 2.5, 7.5, and 15 mg/kg every 12 hours for 14 days. Doxycycline at the doses of 0.75, 2.5, 7.5 and 15 mg/kg and ciprofloxacin at the dose of 30 mg/kg were used as positive controls. Mice were followed for 41 days post infection, and percent survival was determined.

Figure 2:
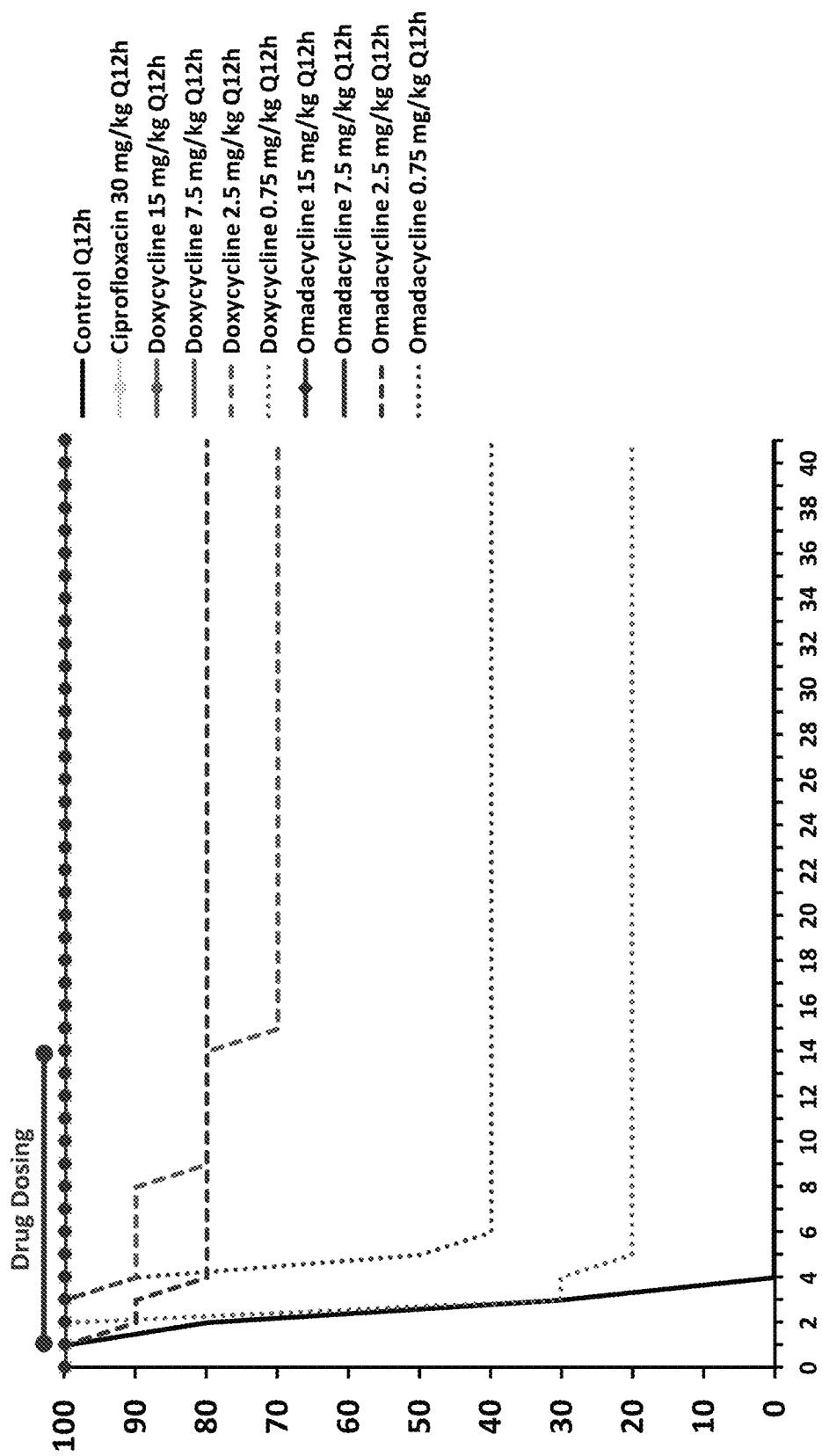

The results are presented in FIG. 2 which demonstrates that Compound A is as effective as doxycycline or ciprofloxacin at treating *B. anthracis* infection for at least 41 days post-infection. In this experiment, MIC for Compound A was <0.03 μg/mL, while MIC for both doxycycline and ciprofloxacin is 0.03 μg/mL. Also, $PD_{50}$ for Compound A was 0.8 (range of 0.6 to 1.1 mg/kg), while $PD_{50}$ for doxycycline was 2.0 (range of 1.4 to 2.6).

Example 9

The in vivo activity of Compound A (omadacycline) was tested in lethal *B. mallei* post exposure prophylactic (PEP) infection model. BALB/c 6-8 week old female mice were infected by 59.6 $LD_{50}$s of *B. mallei* (China 7) via whole body aerosol. Ten mice per each group were used. Compound A was administered intraperitoneally twenty-five hours post-infection at the doses of 0.75, 2.5, 7.5 and 15 mg/kg every 12 hours for 21 days. Doxycycline at the concentrations of 0.75, 2.5, 7.5 and 15 mg/kg and azithromycin at the concentration of 15 mg/kg were used as positive controls. Mice were followed for 55 days post-infection, and percent survival was determined.

Figure 3:
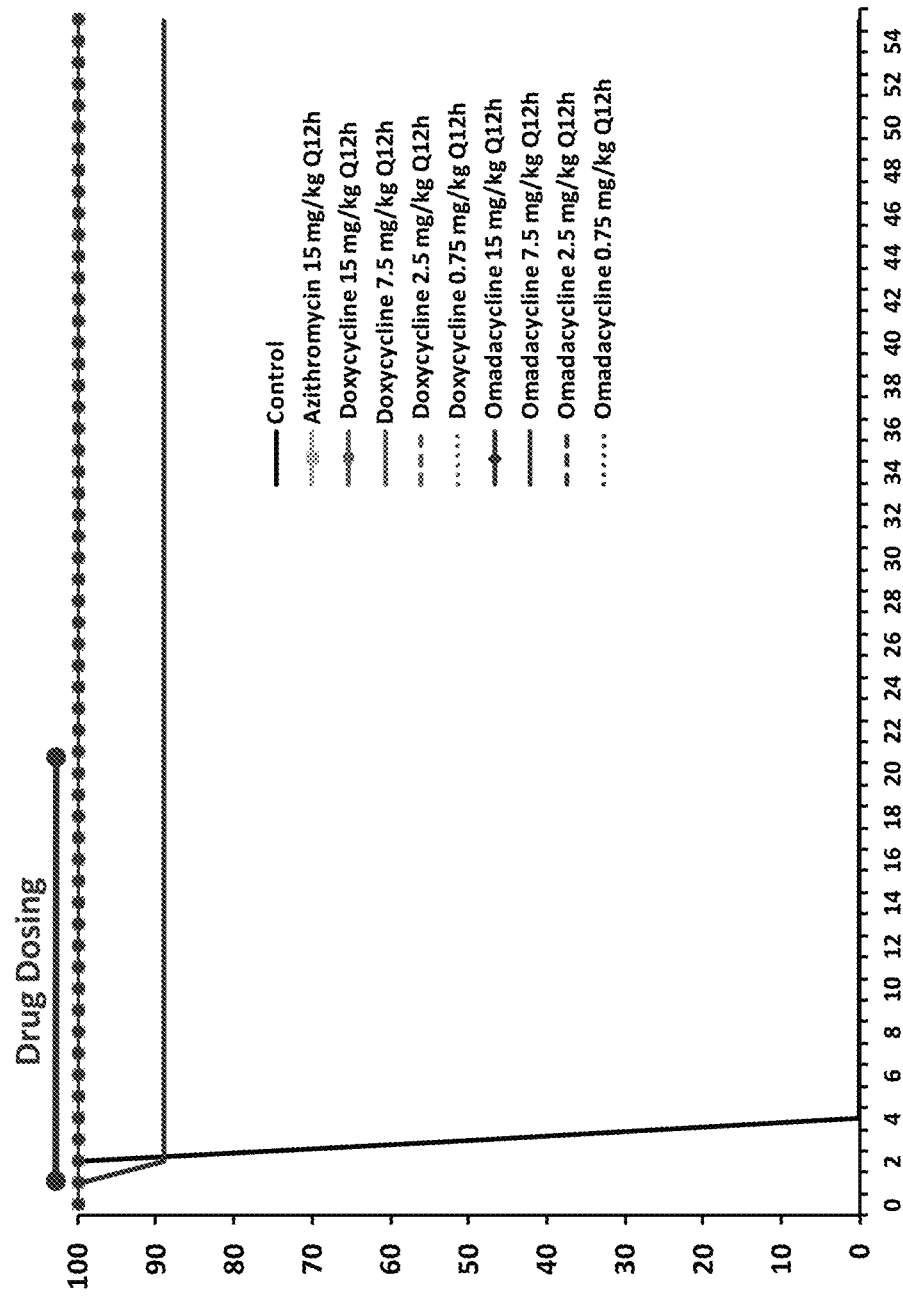

The results are presented in FIG. 3 which demonstrates that Compound A is as effective as doxycycline or azithromycin at treating *B. mallei* infection. In this experiment, MIC for Compound A was 0.25 μg/mL, for doxycycline was 0.06 μg/mL, and for azithromycin was 0.5 μg/mL. Also, $PD_{50}$ for Compound A was <0.75 mg/kg, and $PD_{50}$ for doxycycline was also <0.75 mg/kg. All of the dosing group animals except one survived all treatments. No control group animals survived.

EQUIVALENTS

Those skilled in the art will recognize, or be able to ascertain using no more than routine experimentation, many equivalents to the specific embodiments and methods described herein. Such equivalents are intended to be encompassed by the scope of the present invention. All patents, patent applications, and literature references cited herein are hereby expressly incorporated by reference.

What is clamed is:

1. A method of treating or preventing a bacterial infection in a subject in need thereof, said method comprising administering to said subject an effective amount of a compound, or a salt thereof, at a dose of about 25 mg to about 600 mg administered orally, or a dose of about 25 mg to about 300 mg administered intravenously, wherein the compound is Compound A' represented by the following structural formula:

(A')

[Chemical structure of omadacycline]

wherein said bacterial infection is caused by a bacterium which can be used as a biological weapon, wherein said bacterium is of a bacterial species *B. anthracis*; wherein said bacterium is in the form of a powder or an aerosol, such that said infection in said subject is treated or prevented.

2. The method of claim 1, wherein said bacterium is resistant to antibiotics that are typically used to treat infections caused by the bacterium.

3. The method of claim 1, wherein said bacterium is in the form of spores.

4. The method of claim 1, wherein said compound is administered once per day or twice per day.

5. The method of claim 1, wherein said compound is administered orally at the dose of about 25 mg to about 600 mg.

6. The method of claim 5, wherein said compound is administered orally at the dose of about 300 mg or about 600 mg.

7. The method of claim 1, wherein said compound is administered intravenously at the dose of about 25 mg to about 300 mg.

8. The method of claim 7, wherein said compound is administered intravenously at the dose of about 100 mg, about 200 mg or about 300 mg.

9. The method of claim 1, wherein the method comprises administering said compound for at least 3 days, at least 7 days, at least 14 days, at least 21 days, at least 30 days or at least 60 days.

10. The method of claim 1, wherein the method comprises administering to the subject one or more loading doses of the compound, followed by one or more maintenance doses of the compound.

11. The method of claim 10, wherein the one or more loading dose is greater than the one or more maintenance dose.

12. The method of claim 10, wherein the loading dose is about 200 mg and the maintenance dose is about 100 mg.

13. The method of claim 10, wherein the loading dose is about 400 mg and the maintenance dose is about 300 mg, about 200 mg or about 100 mg.

14. The method of claim 10, wherein the loading dose is intravenous and the maintenance dose is oral.

15. The method of claim 10, wherein the compound is administered as an intravenous loading dose of 100 mg twice daily, followed by an intravenous maintenance dose of 100 mg once daily.

16. The method of claim 10, wherein said compound is administered as an intravenous loading dose of 100 mg twice daily, followed by an oral maintenance dose of 300 mg once daily.

17. The method of claim 10, wherein said compound is administered as an oral loading dose of 300 mg twice daily, followed by an oral maintenance dose of 300 mg once daily.

18. The method of claim 1, wherein said subject is a human.

* * * * *